United States Patent [19]

Zimmerman et al.

[11] Patent Number: 5,199,439

[45] Date of Patent: Apr. 6, 1993

[54] MEDICAL STATISTICAL ANALYZING METHOD

[76] Inventors: Stanley Zimmerman, 501 Cumberland Rd. E., Mobile, Ala. 36608; Lonnie Brown, 18 Rickarby Pl., Mobile, Ala. 36606; Steven Zimmerman, 4151 Bay Front Rd., Mobile, Ala. 36605

[21] Appl. No.: 465,049

[22] Filed: Jan. 16, 1990

[51] Int. Cl.$^5$ ............................................. A61B 5/02
[52] U.S. Cl. .............................. 128/670; 364/413.02
[58] Field of Search ............... 128/670, 668, 731, 733, 128/734; 364/413.02, 413.03, 413.05

[56] References Cited

U.S. PATENT DOCUMENTS

| 4,197,854 | 4/1980 | Kása | 364/413.03 |
| 4,665,499 | 5/1987 | Zacharski et al. | 128/731 |
| 4,815,474 | 3/1989 | Duffy | 128/731 |

OTHER PUBLICATIONS

Walter A. Shewhart, Ph.D., *Statistical Method from the Viewpoint of Quality Control*, (c) 1939, pp. 1–49.
Donald DelMar, George Sheldon, *Introduction to Quality Control*, (©) 1988, pp. 123–143.
Irvin W. Burr, *Statistical Quality Control Methods*, (©) 1976, pp. 23–35.

*Primary Examiner*—Francis Jaworski
*Assistant Examiner*—George Manuel
*Attorney, Agent, or Firm*—Gregory M. Friedlander

[57] ABSTRACT

A method of using existing and new hardware in order to derive statistical information and control charts reflecting statistical changes in a monitored individual utilizing patient monitoring devices, communications between patient monitoring devices and computer systems. The process involves (1) selection of data from the stream of data originating from the monitoring device, (2) compartmentallization of data into records, (3) selection and isolation of that portion of each selected record related to the monitored event (e.g. blood pressure), (4) determining for significantly statistical consecutive groups, the average average, and the standard deviation (sigma) (5) repeating the said process steps 1 through 4 after a delay in order to avoid covariance until, after a significant number of repetitions, the number of which are selected by the user, it is possible to set control chart limits (upper and lower control limits and the theory of runs), (6) setting control limits (the upper control limit and lower control limit are functions of sigma, usually the same, and adjustable by the user) (7) to set up appropriate control charts on a moving screen (either internally or on displays); (8) continuously determining average-average and standard deviation as set out in steps (1) through (4) above; (9) continuously graphing and displaying sigma, x-bar and range against the control charts; (10) marking statistically significant deviations on the chart as by circling readings which deviate farther than the control limits and where the theory of runs, as controlled by the user, indicates a statistically consistent number of deviations on one side of the average for each chart (11) readjusting the x-double bar (or center line of the x-bar chart) and sigma as set out in steps (1) through (4) above and/or the R chart sigma bar (center line) and control limits as needed during the process (12) and restarting steps (5) through (12); (13) sending data from an isolated portion of said control chart to a database; (14) comparing the isolated portion to the database collection of similar segments and categorizing the same; (15) matching said categorized portions to accepted treatments and diagnosis, (16) grouping such sets of treatments and diagnosis with the corresponding portions sent by the user and (19) displaying on the screen in response to a request from the user the accepted options as to diagnosis and treatment.

38 Claims, 28 Drawing Sheets

(25) Establishing Communications between a medical instrument and a microcomputer using techniques known in the art

(26) Determining the medical data to be monitored, stored, analyzed, displayed as controlled charts. This is done by selection by a medical doctor of what information should be monitored in a patient.

(27) Determining the medical data to be monitored, stored, analyzed and displayed

(28) Creating a procedure to identify, isolate and capture the relevant data within each data record.

FIG. 10

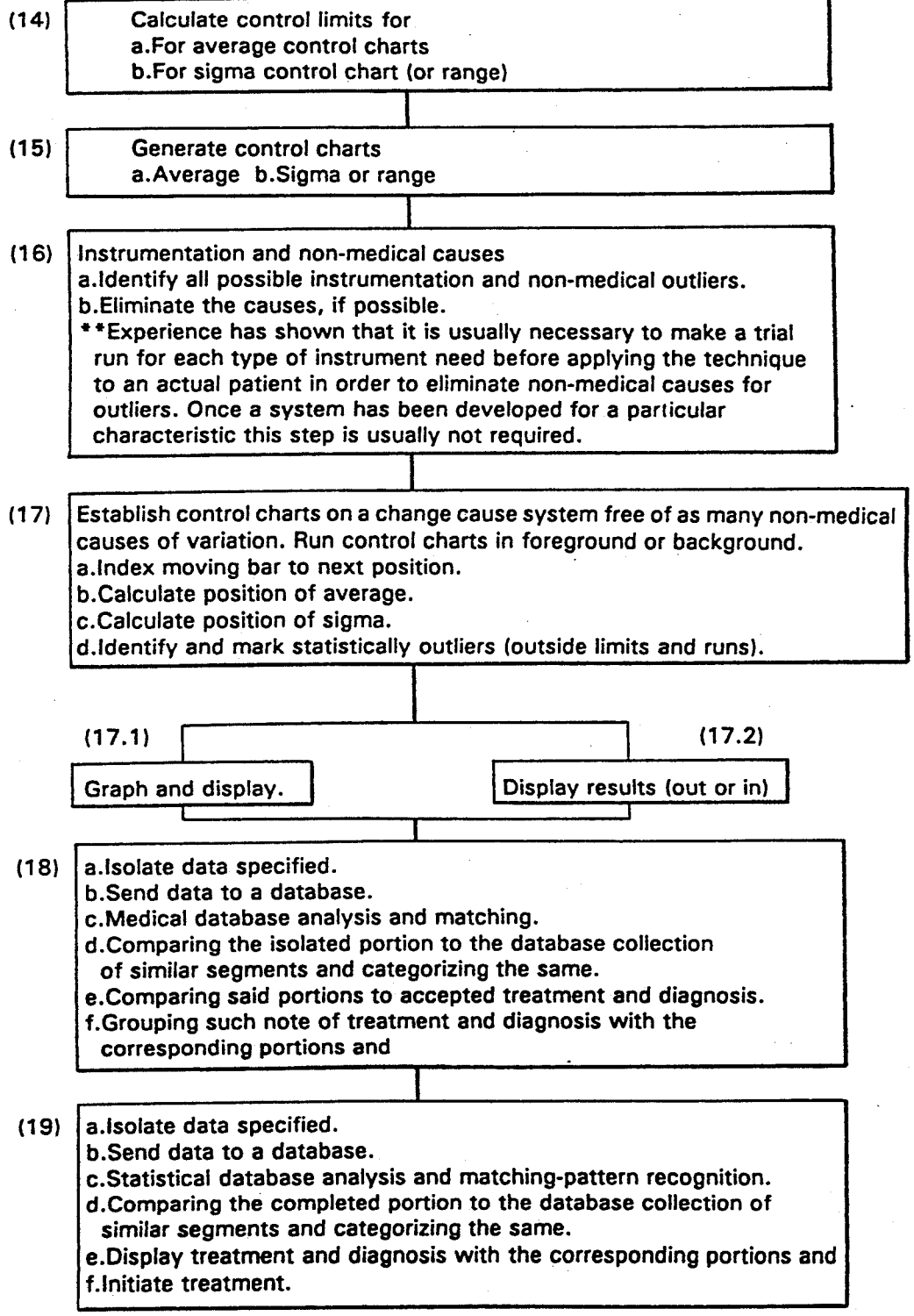
FIG. IIB

MEDICAL STATISTICAL ANALYZING METHOD

BACKGROUND OF INVENTION

Prior Art

This invention applies to statistical devices.

More particularly, this invention applies to medical statistical devices or devices using statistics in a medical environment.

More particularly, the invention applies to obtaining statistical information in control charts, for monitoring and analysis of medical processes.

Statistical analysis using Shehwart type process control charts was developed approximately 40 years ago in its present form. The use of statistics generally in medicine probably dates back to the early use of the scientific method in determining causes. Statistics are currently kept for purposes of disease control and diagnosis. The shortcoming of prior art in this area is not the failure to use accepted statistical techniques, but the failure to treat a medical patient as a true process. In any process, it is unacceptable to have an inflexible standard set because of the number of changes and steady states possible in any situation.

One example of statistical analysis in a medical environment is found in Bell, et al.; U.S. Pat. No. 3,322,954; which relates to diagnosis of statistically significant variations of radiation.

The use of inflexible standards in a statistical situation using central processing units is also known in the medical field. Hutchins; U.S. Pat. No. 4,583,524; processes information in order to obtain medical diagnosis or treatment. Hrushesky; U.S. Pat. No. 4,519,395; shows the use of statistically analyzed mean and standard error in heart rate. It foresees the monitoring of not only the patient, but the addition of drugs to the patient over time. Similarly, John; U.S. Pat. No. 4,545,388; shows the application of basic statistical computation of mean and variance and comparison to a previously obtained self norm for a given individual. Both of these patents substitute the use of statistically inflexible standards for medical judgment and provide signals relative to the change. Both fall short of the current invention by failing to provide for process charts and following the various stable states in the course of a patient's treatment. These patents substitute limited information to the information provided by Shehwart type process control charts which signify change over time and provide a continuous and monitorable statistical analysis.

Hrushesky and John address the broad aspects applicable to basic determinations of the idea of finding statistically significant changes in mean and standard deviation or variance measurements. Because neither use control chart tracking of a patient, the prior art patents are limited to situations where a known norm is available and where the patient is controlled only by attempting to reach the given norm.

The present invention allows for the variations necessary to follow a patient who does not have a norm, and perhaps never will, during the medical intervention process. The present method treats the patient as an ongoing process with the examination being directed to changes in the process and stabilizing or maneuvering the process in any given direction. The use of control charts allows the physician to set a given norm for a patient regardless of the patient's current condition or records kept on the patient.

The present invention addresses the question by giving a graphical analysis which is continuously monitorable by the physician and wherein the limits may be adjusted to allow the user to reset the analysis as a given patient changes.

Typical medical devices using current technology only give indicators or alarms of problems which show single events out of the ordinary when a patient's condition has already become unstable. Prior art was designed in order to have machines assist in the practice medicine for the doctor. Since medicine is a less than certain science, this results in equipment which does not serve a consistently useful function statistically.

Other existing equipment and methods provide a graph format but without statistical analysis, merely provide graphing of raw data. The present process allows for obtaining statistically significant historical analysis of the varying conditions, medicine, and equipment used for treatment.

One purpose of this invention is to provide a physician statistical information on a patient and to present the information in an interpretable form to a physician/statistician at a constant rate with sufficient statistical information being provided at one time to have statistical signicance.

Another purpose of the method is to provide an early warning system for medical patients. This process will enhance the early recognitions of problems with medical patients while being monitored with various equipment.

Another purpose is to provide an early warning system which will enable the physician to reduce the probability of the patient's going into unstable conditions. This process will also enable physicians to determine the stability of a patient for the process of discharging from hospital stay.

Another purpose it to provide a process with the capability to interface computers to medical devices. the process will use serial port communications from medical devices to a computer. The computer will then statistically analyze data received from the medical device and graphically display the statistical analysis of this data. This analysis of data will enable the physician or clinician to detect early indicators of non-stable conditions for the patient.

Another purpose is to provide for alarm systems based on an unknown patient; they are not individualized. The statistical analysis and graphics are based on an established normal for the individual. Mathematical laws and statistical formulas establish control limits for the patient based on the normal values for a particular patient.

Another purpose is to provide a method of statistical analysis which will provide statistically significant information about medical equipment and medications applied during the monitoring period.

These and other objects and advantages of the invention will become better understood hereinafter from a consideration of the specification with reference to the accompanying drawings forming part thereof, and in which like numerals correspond to parts throughout the several views of the invention.

BRIEF DESCRIPTION OF THE DRAWINGS

For a further understanding of the nature and objects of the present invention, reference should be made to the following detailed description taken in conjunction with the accompanying drawings in which like parts are given like reference numerals and wherein:

FIG. 10 is a block diagram of the process steps for setting up hardware utilized in collecting data for the invention.

FIG. 11B is a block diagram of the process steps 14-19 used for setting up a system used by the invention and of the process used for collecting data and establishing control charts used by the invention.

GENERAL DISCUSSION OF THE INVENTION

Figure 1:
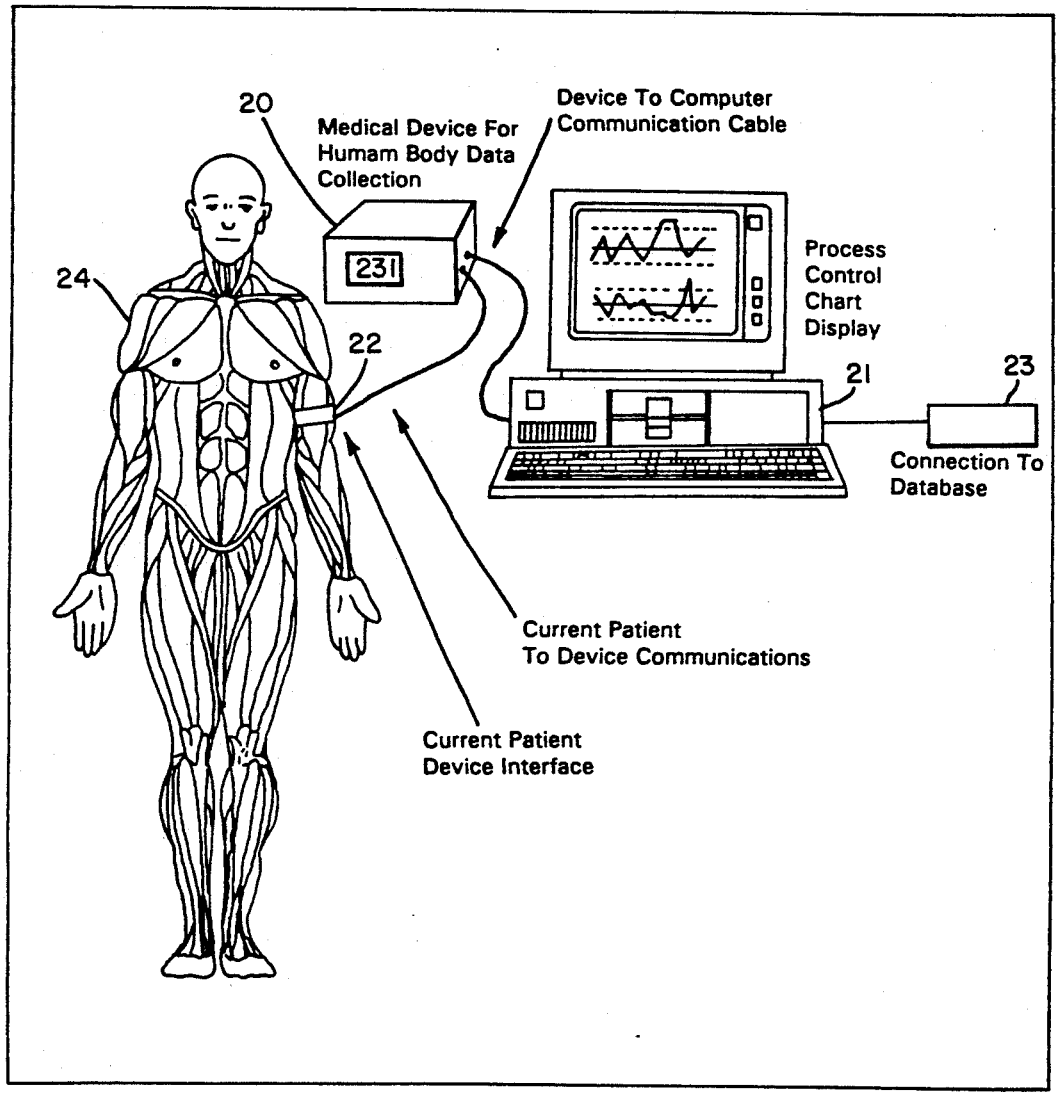
FIG. 1 is a plan view of a patient monitored by the the invention.
Figure 2A:
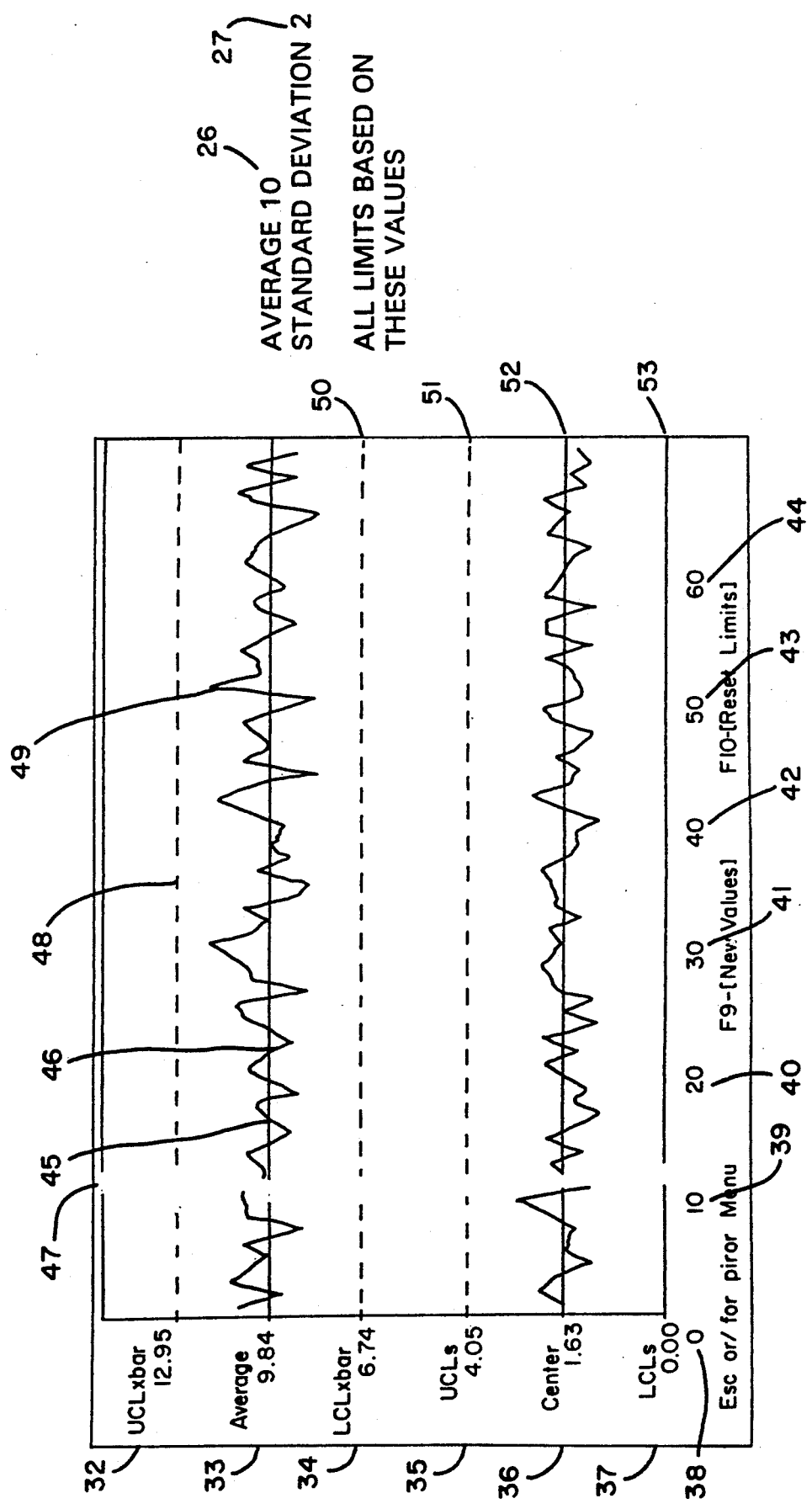
FIGS. 2A, 2B, and 2C are a graphical representation of a set of three charts generated by the system showing the effect of a change of average without a change of standard deviation.
Figure 2B:
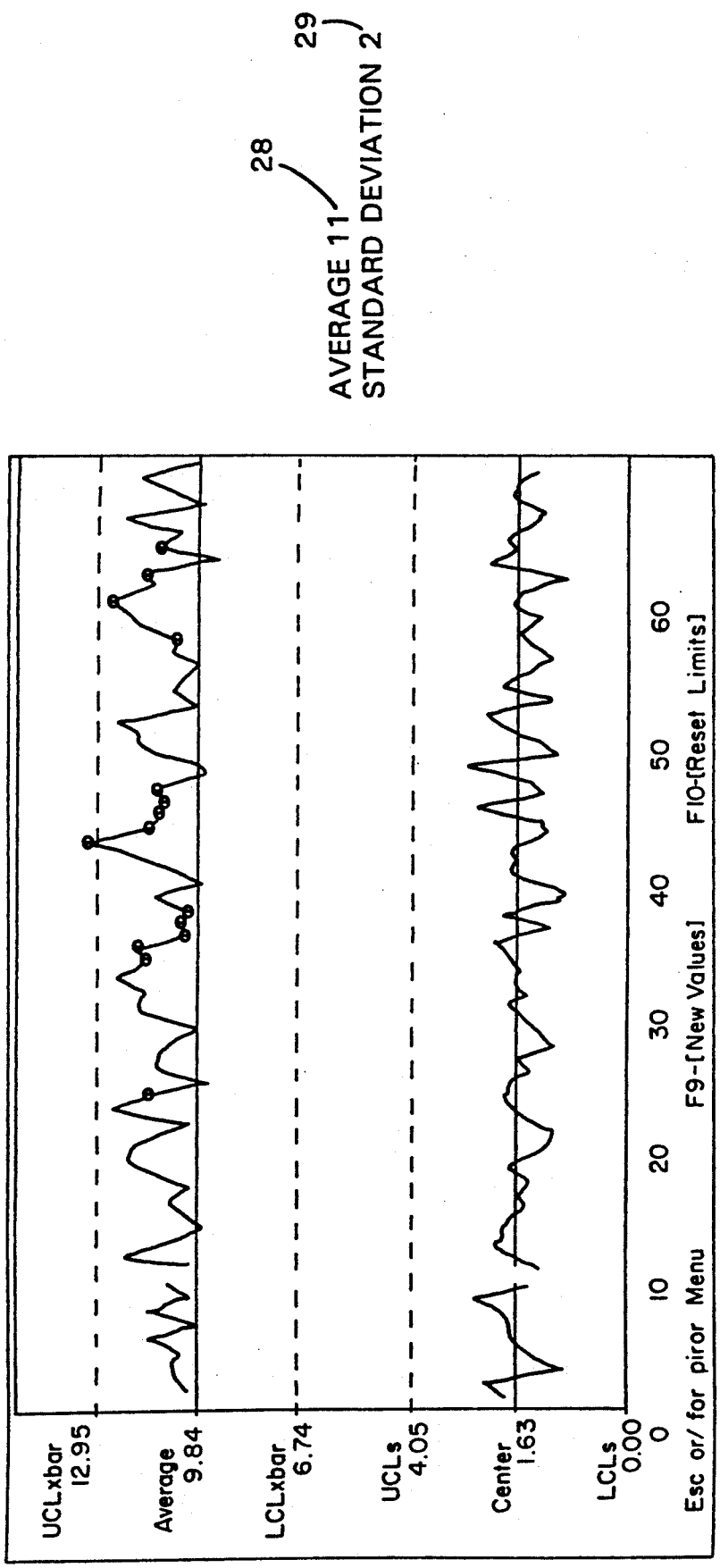
Figure 2C:
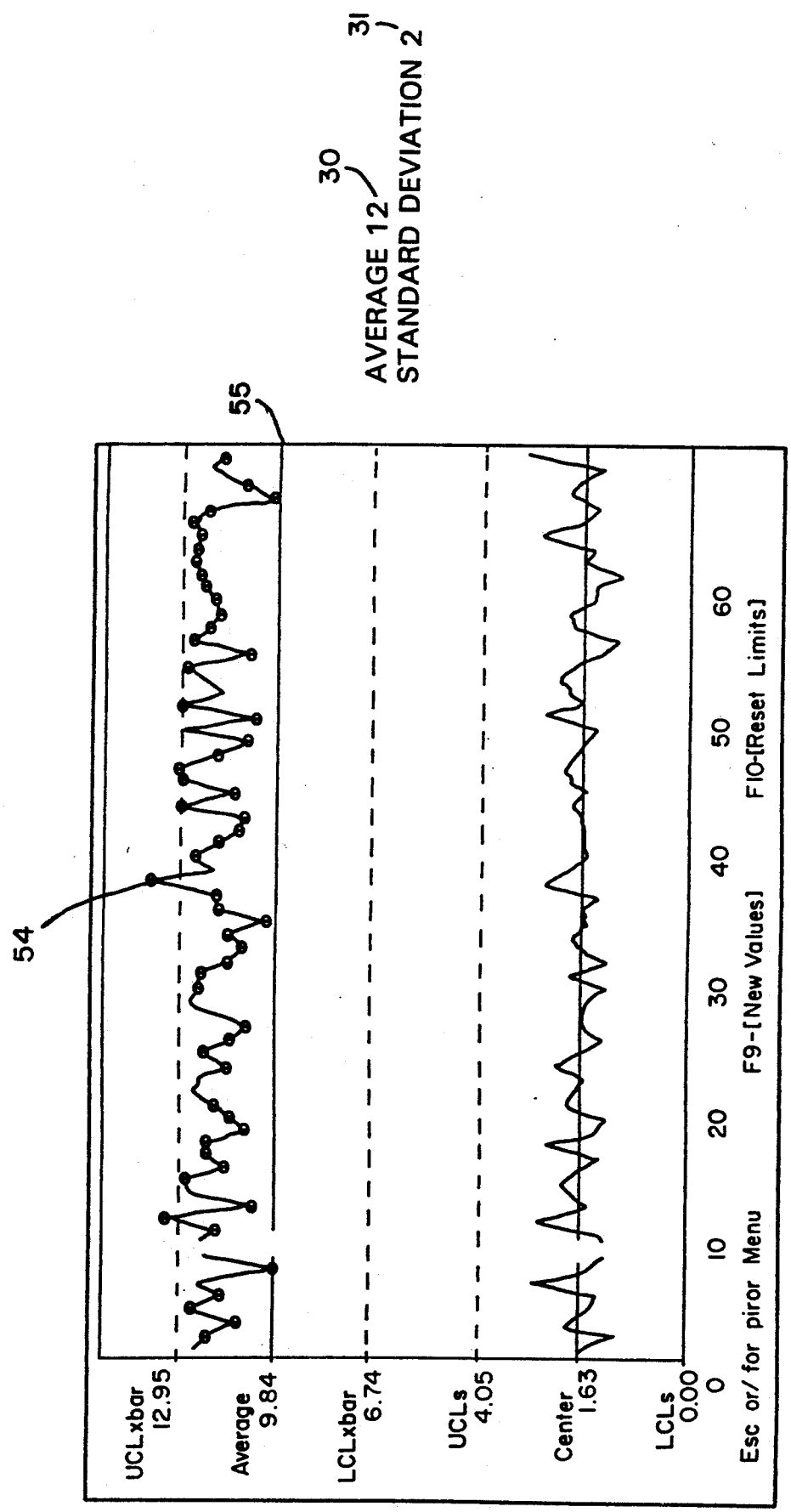
Figure 3A:
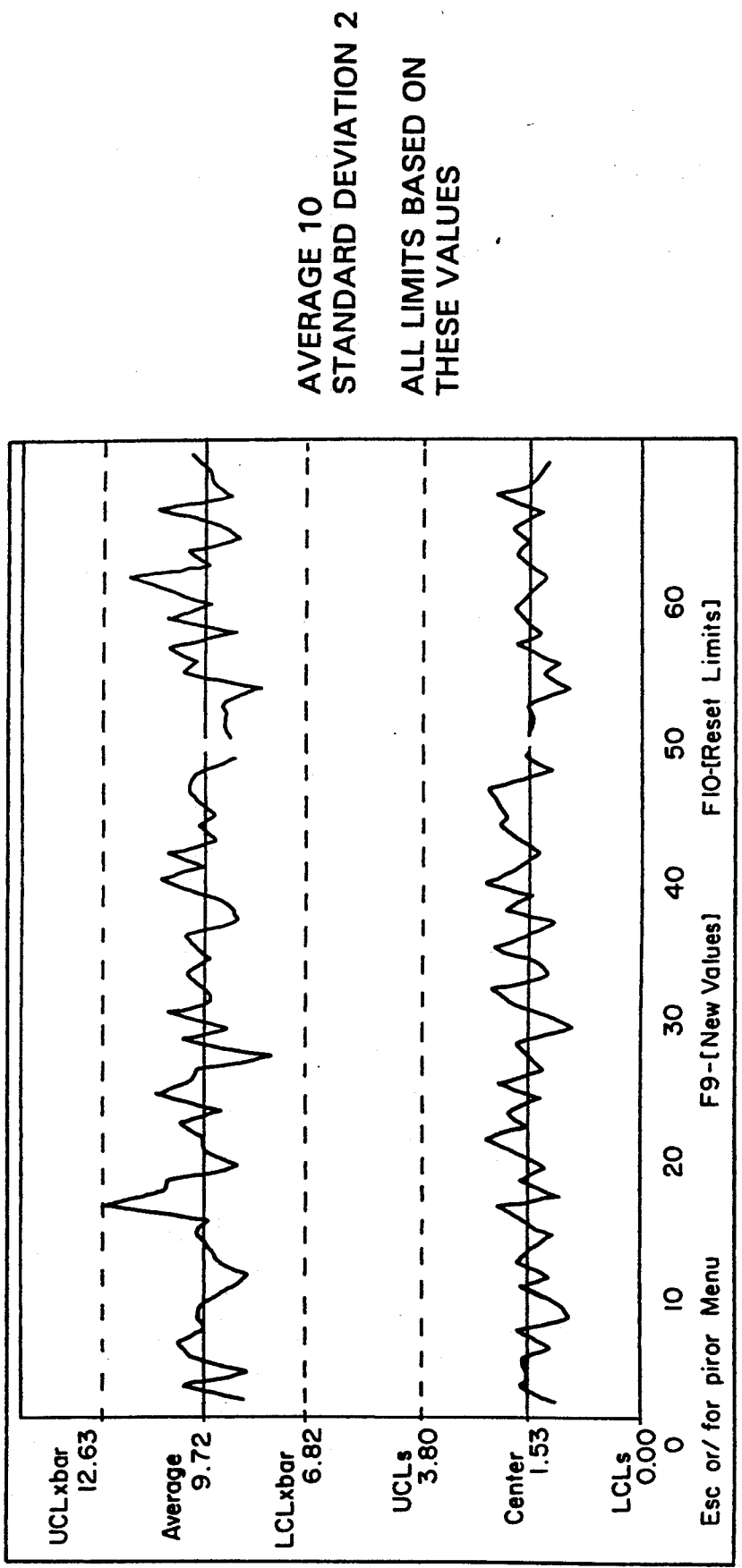
FIGS. 3A, 3B, and 3C are a graphical representation of a set of three charts generated by the system showing the effect of a change of standard deviation without a change of average.
Figure 3B:
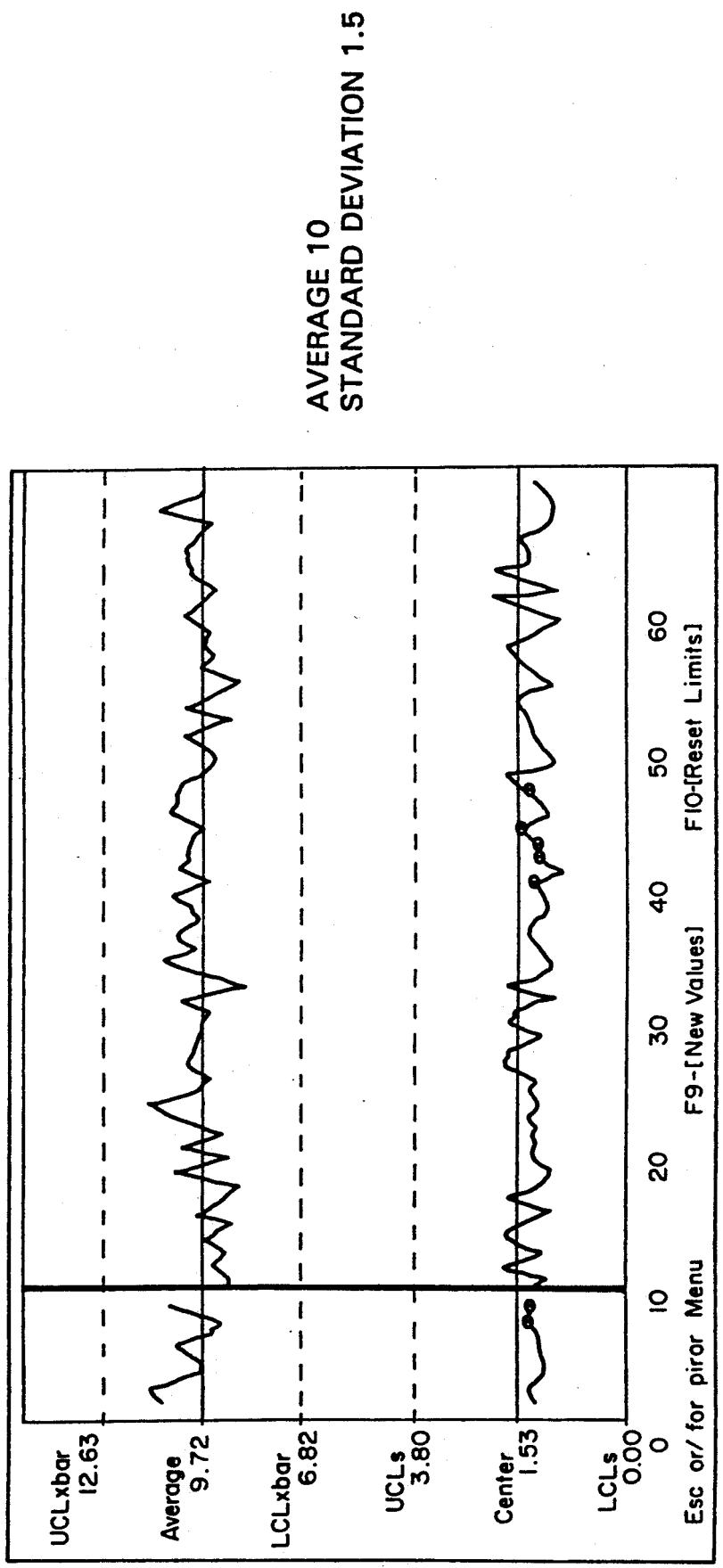
Figure 3C:
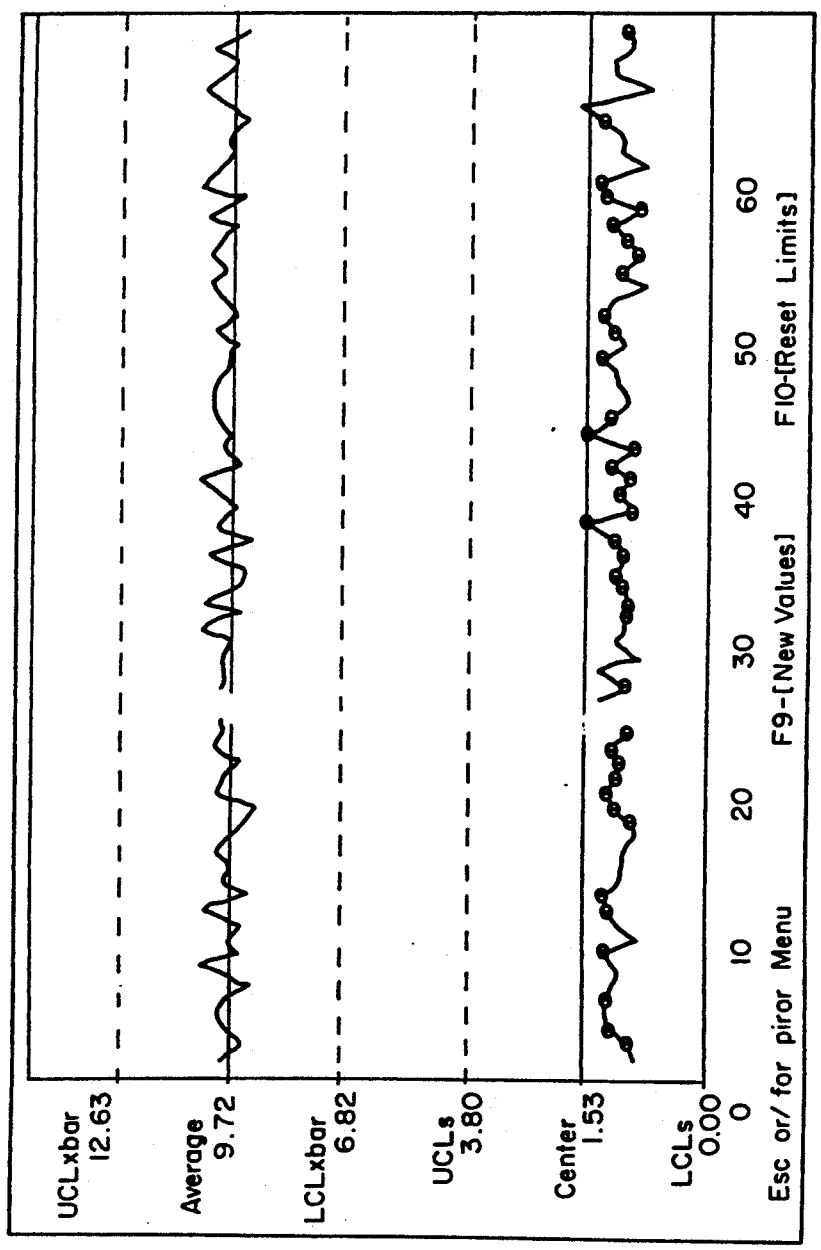
Figure 4A:
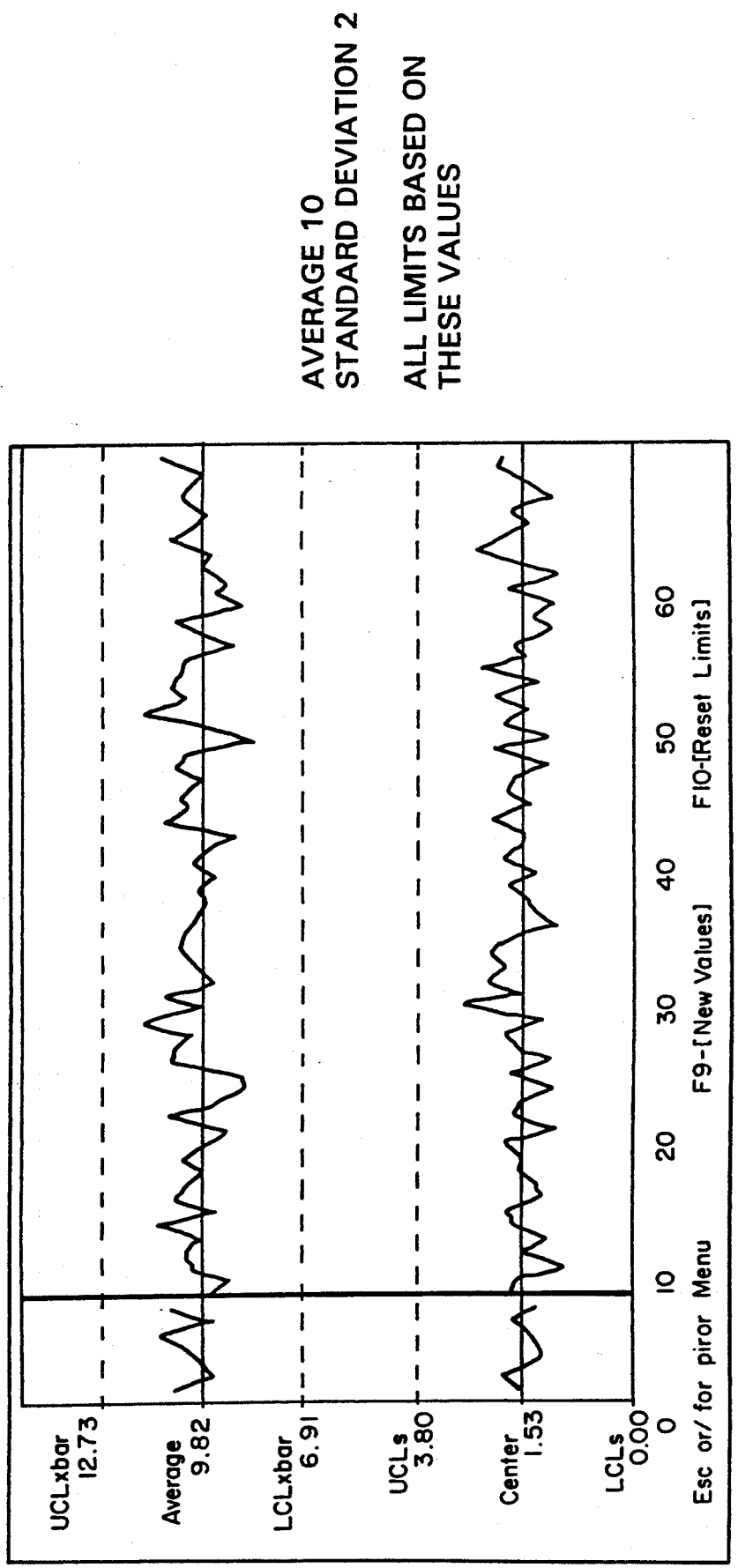
FIGS. 4A, 4B, and 4C are a graphical representation of a set of three charts generated by the system showing the effect of a change of standard deviation with a change of average.
Figure 4B:
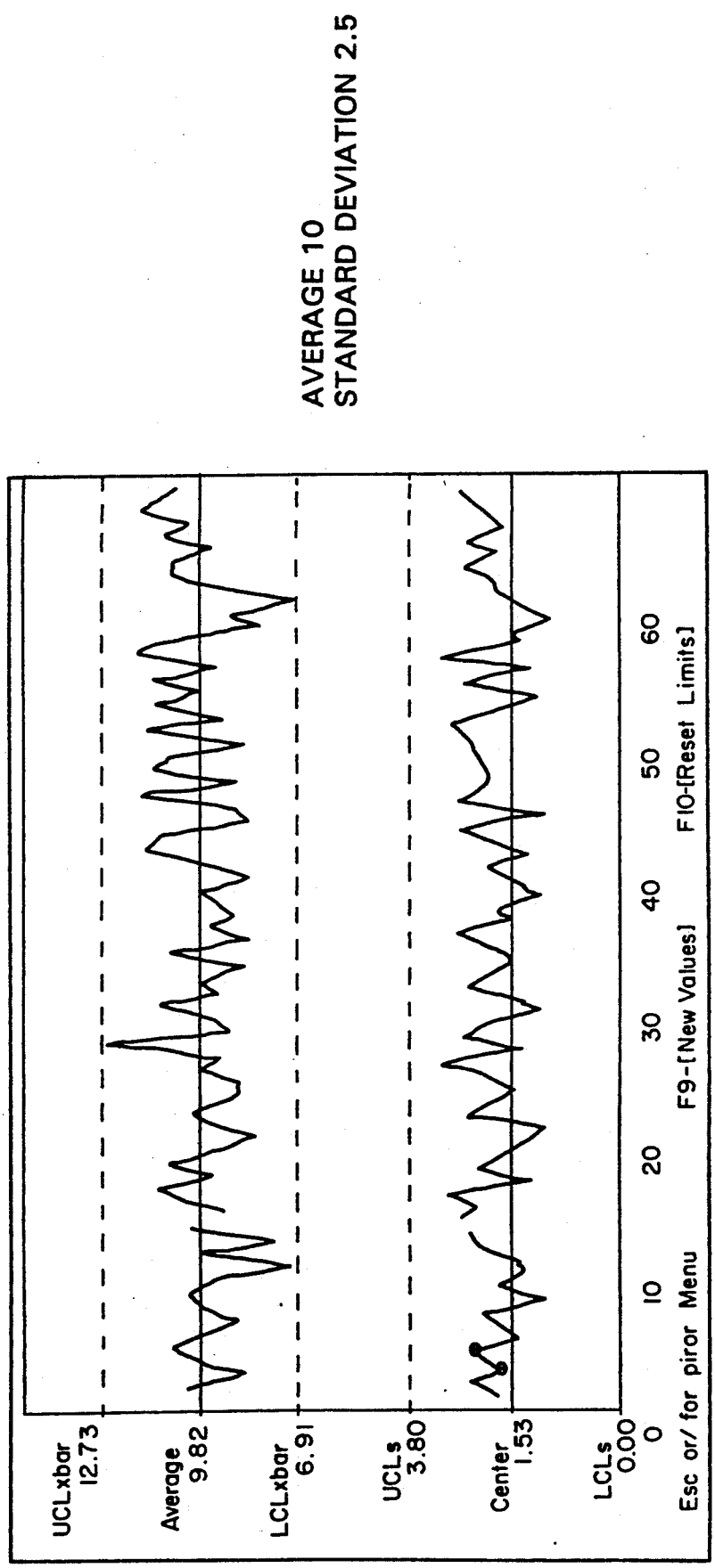
Figure 4C:
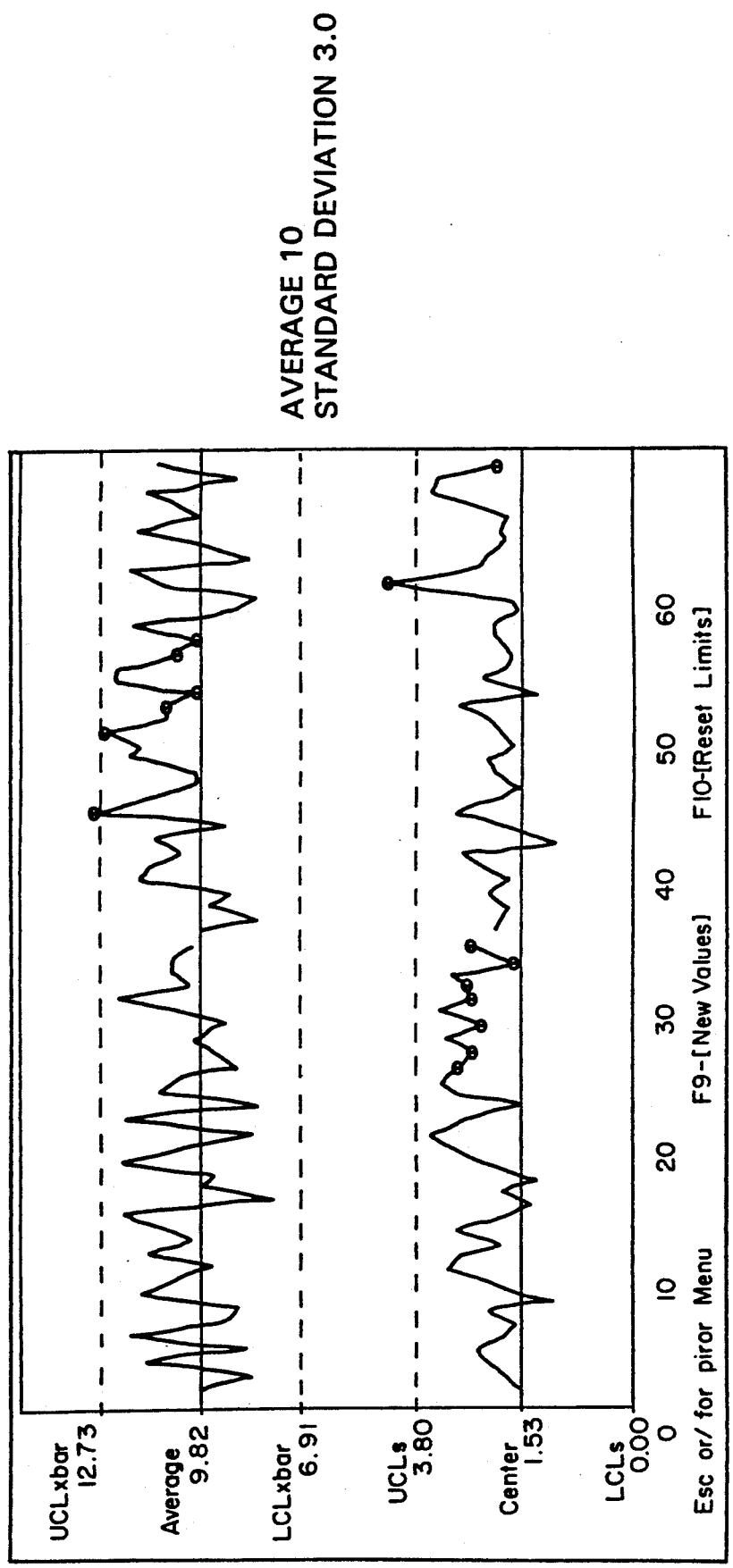

The system includes hardware including patient interfaces with medical devices, communication cables to medical devices, the medical device itself, communications devices from the medical devices to computers, the computer equipment which receives the cable from the medical device, a separate input to record on a time coordinated basis treatment into the computer from an operator or from automatic treatment equipment.

The equipment also utilizes software which includes a data communication software, storage software, statistical analysis software, display software for process control charts, time dating software, and software for communication with the host database and for getting replies from the host database where the host database comprises data which has been previously analyzed statistically relative to a large number of patients.

The software is an integral part of a network which acts on readings from a patient in order to produce a readable analysis of the patient's condition.

Medical devices using current technology only give indicators or alarms of problems when a patient's condition has already become unstable. An example of this is a normal alarm for patient heart rates, or a rate of 40, which is an indicator of bradycardia of a patient, or a rate of 140, on the high end, which is an indicator of tachycardia of a patient. When these alarms are violated, the patient is already unstable, resulting in treatment by the use of drugs or the use of medical devices. It has been documented in medical journals that the treatment with medical devices such as a defibrillator to return a patient to stability causes damage to the heart muscles. This invention uses statistical analysis of heart rate that a physician would be able to recognize as an indicator of an unstable condition earlier than he would with normal alarms. This indicator would allow the physician to treat the patients with drugs or medication and not more extreme medical devices such as a defibrillator. This would result in less long-term damage to that patient's heart.

Prior art which simply reads if a continuous number of elements fall outside set limits fail to give an adequate amount of information to someone using this for statistical analysis purposes. This invention uses the theory of runs to analyze where a significant number of deviations fall on a given side of the average for a control chart. The number which is statistically significant is set in step 6.

Another example is the use of a patient's temperature. The indicators of a patient's temperature are typically not monitored by an alarm, and only viewed randomly by the clinicians. An increase in a patient's temperature is an indicator of a patient having an infection. The use of graphics display and statistical analysis of temperature can result in an early warning of a potential infection. This would allow the doctor to possibly totally eliminate the infection or reduce the effect on the body of an infection.

Another application is interfacing to pulse oxymetry. Pulse oxymetry is used to measure the oxygen concentration in the bloodstream of a patient. Normal alarm conditions are preset at a rate of 90% oxygen saturation. Once the patient has reached a level of 90% oxygen saturation, there is an immediate need for oxygen to be administered to the patient or permanent damage to the patient will occur. Through the use of our statistical analysis and graphics display, an early indicator of reduction in oxygen saturation will occur, thus allowing the physician to utilize oxygen treatment prior to the patient going into duress and having possible damage.

Another application is for the monitoring of invasive blood pressure during surgical procedure. Invasive blood pressure during surgical procedures are normally monitored with no alarms and are observed for radical changes by the anestheslologist in the case. Typically, when a large change occurs, the anestheslologist will be forced to administer high amounts of drugs or make a large change in the anesthetizing agent which is used to keep the patient unconscious during the procedure. Through the use of our statistical analysis and graphic display, the anestheslologist is allowed to recognize the changes in the patient earlier. This early recognition allows the anestheslologist to control the patient with a smaller dosage of medication or a lesser percentage of anesthetizing agent. It is documented in many medical Journals that long-term health is increased with a reduced amount of medications or a reduced amount of anesthetizing agents.

Another application of the statistical analysis is in the use of laboratory results on the patient, such as Ph level or oxygen level. Typically, laboratory results are looked to be within a very wide window and are treated to be either acceptable or unacceptable. By the use of the statistical analysis and graphic display in this method, as a change occurs in a particular patient that is outside of 3 standard deviations for that particular patient, an early indicator of potential problems with the patient is announced.

Examples of specific types of equipment that can be interfaced are:
1. Patient physiological monitors, which include the monitoring of heart rate, pulse rate, respiration, non-invasive blood pressure, invasive blood pressure, and temperature.
2. Pulse oxymetry, which monitors oxygen saturation ($SAO_2$), and pulse rate.
3. Non-Invasive blood pressure apparatus.
4. Devices for the measuring of oxygen.
5. Devices for the measuring of carbon dioxide.
6. Capnograms.
7. Devices for the measurement of entitled carbon dioxide.
8. Devices which electronically measure urine output.
9. Devices which measure temperature.

DETAILED DISCUSSION OF THE PREFERRED EMBODIMENT(S)

The purpose of the invention is in order to allow for the application of quality control concepts to existing equipment used in a medical environment.

Typically, the equipment which exists in a medical environment produces data which is in digital form in the form of ASCll, or else is an analog form which can be translated to digital by any number of means which are known in the art of analog to digital conversion.

For purposes of the discussion, it is assumed that the signals are digital signals and that the conversion step is unnecessary, although the use of the invention with an analog signal to a digital signal for purposes of this would be identical except for the added step of conversion.

In order to avoid confusion, numbers referencing drawings appear in numeric form and numbers otherwise used in describing the invention are typed out alphabetically.

Communications between computer equipment usually require at least three pins, but may use twenty-five-pin standard communication port, which is present on most modern medical analysis or reading equipment.

For purposes of this invention, the data which is received is sent through pins which are provided on the equipment to an outside source, but the same technology would apply if the data was used internally in the machine or medical equipment itself and the medical equipment was supplied with screens and the other components necessary in order to effectuate the invention.

It is noted that any single piece of medical equipment may send out several different medical bits of information, for example, blood pressure readings and temperature, and in addition may have control characters added to the readout from the existing equipment.

The first step of the process, therefore, is to take the data which is coming in blocks which can include control characters, temperature and blood pressure together and separate out the specific data to be used utilizing methods known in the art from the blocks of data.

The entire process can be described in steps, with the first step being the selection of standards. These standards may be from a present group.

Other information may be desired which could include selecting the statistical method to be used. The types of methods available, generally under this invention which uses control charts would be from the following sets:

| | |
|---|---|
| (a) | Average and sigma charts |
| | Average and range charts |
| | P charts, setting out the percent effective or defective |
| | U charts) |
| | or > defects or defects per instance |
| | C charts) |
| | NP charts - number of occurrences |

In the preferred embodiment, the average and sigma charts only are used. The use of range charts is also set out parenthetically as an alternative to the sigma chart. It is to be noted that statistically the range chart is only an approximation and in the preferred embodiment would not be used.

In utilizing the invention, the first step is the set up of hardware. Referring generally to FIG. 10 this is accomplished by establishing communications step 25 between hardware shown in FIG. 1 as the medical instrument 20 and microprocessor 21 and database 23. This assumes the existence of communications between patient 24, through medical device interface 22 and medical instrument 20.

Referring again to FIG. 10, determining (by mental operation of the user) the medical data to be monitored, stored, analyzed and displayed rs control charts is determined Step 26 from the data coming as digital signals output by the specific monitoring equipment. The determination is a selection by the user of the specific condition, (e.g. temperature, blood pressure, etc.) to be monitored using the invention. Next, determining the data record from the data coming into the system is isolated step 27 using data block separation techniques known in the art. Finally, in the hardware set up, creating the procedure to identify, isolate and capture the relevant data within each record from known techniques for working with computer signals is step 28. This type of hardware set up is commonly used by existing equipment. One difference from the present invention from existing equipment is merely the isolation of the information for modification in the process steps which follow.

Figure 11A:
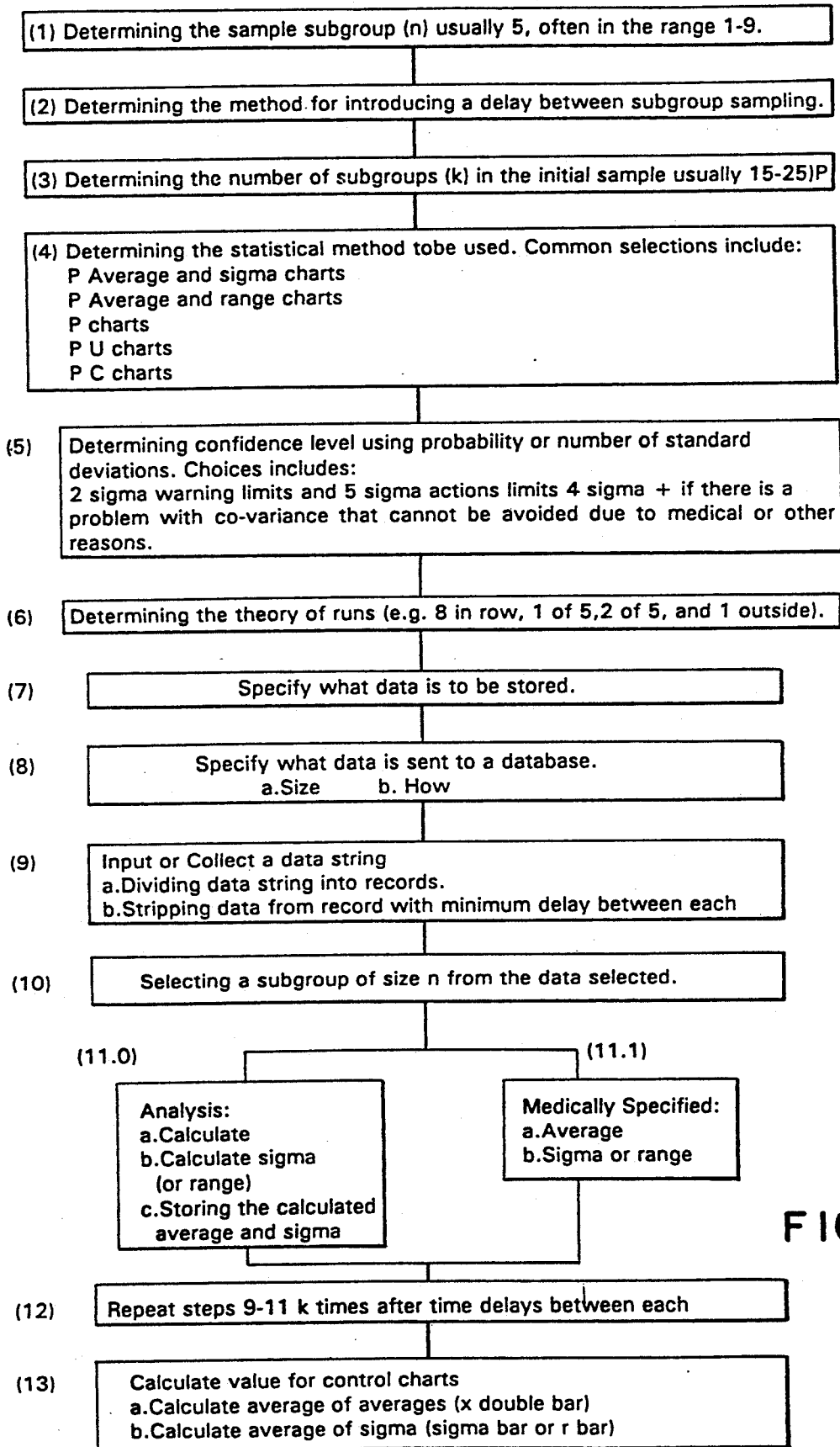
FIG. 11A is a block diagram of the process steps 1-13 used for setting up a system used by the invention and of the process used for collecting data and establishing control charts used by the invention.

Subsequent to hardware setup, the system must be set up as shown in FIG. 11A and FIG. 11B. Standards are determined. Determining the standards include the sample subgroup step (1), (Referred to as N in algorithms used herein); (2) determining the method for introducing delay step 2 between subgroup samples step 1 by programming techniques or by having delays built into the computer equipment based on the need for statistically significant delays between samples as is known in the art; the number or set of subgroups or repetitions of subgroups in the initial sample step 3 (Referred to as K in algorithms used herein).

The set step 3 of subgroups step 1 are used in the preferred embodiment for determining the average average (x-double bar) and average standard deviation (sigma bar).

Also in the setup, the user must determine the statistical method to be used 4. As indicated, the statistical method to be used is usually average and sigma charts (other options would include average and range charts, p charts, u charts or C charts).

Also in the setup, the user must determine the confidence level step 5 for the control charts using probability or the number of standard deviations. Choices include a factor times the average standard deviation (sigma), the theory of runs as described in more detail below, or similar methods known in the art of statistics.

Standard deviation choices such as TWO sigma warning limits (i.e. marking occurrences which are outside TWO sigma warning limits) and THREE sigma action limits (taking appropriate action for occurrences outside Three Sigma) are examples. Four sigma or higher limits may be used where there are problems with covariance that cannot be avoided due to medical or other reasons.

The theory of runs is determined step 6 and refers to the number of consecutive points graphed on either side of the average either with or without at least a certain number of the points being outside the control limits as set by the confidence level step 5.

In the preferred embodiment, the confidence level or sigma factor step 5 is the same for the upper and lower control limits and for both charts. Varying these levels step 5 so that the upper and lower control limits were different would not materially depart from the inventive concept used herein.

The next step in the system set up is determining the information to be stored step 7 and the information to be sent to a database 23. An example of step 7 would be the selection of the size of the data sample to be sent step 8(a) and whether the sample is automatically sent or to be sent manually step 8(b). In the preferred embodiment the data to be stored step 7 is all of the data and the size of the data to be sent step 8(a) is the 30 points displayed and selection of a data sample step 8(b) is done manually by a particular keystroke on the equipment.

All of the settings set out as in steps 1 through step 7, or any group thereof, could be pre-set into the equipment as a standard for all patients, entered individually, or keyed into the equipment automatically upon determining a given condition of the patient from a selection of conditions on the screen or may be keyed in one at a time.

FIG. 11A and FIG. 11B also outlines data collection and establishing charts. The first step is the input of data step 9. This may be done by hand, for example putting readings from notes or equipment on a time related basis into the system. By handling the input of data in this fashion, the need to separate computer signals, by various methods known to the art, steps 27 and 28, is avoided.

In the preferred embodiment, this second step 9 assumes that the data will come about normally in a single block of data, which may include multiple readings. For example, a single temperature reading, blood pressure reading, and other medical readings, along with a single set of control characters which the monitoring equipment generates for programming reasons internal to the equipment may all come in a block from which the specific data to be graphed is isolated by the techniques set up in steps 27 and 28.

Inputting data step 9, can be broken into steps 9(a) dividing of data into records, stripping data step 9(b) which is the isolation of the datum to be processed, which, for purposes of this discussion, will be assumed to be the temperature, and setting aside the other portions of a given block which could be treated in a similar fashion, except the control characters probably would not be utilized.

Selecting or placing data step 10 of one of a set the number of which is specified in step 3 of a certain number (k) of consecutive subgroups the size of which is specified in step 1 of size n, allows for putting together subgroups which are preferably sets step 1 of four or more stripped data units, but sets of at least one stripped data units as set in step 1.

The number, k, of such subgroups step 1 could be reduced to one for extremely slow readings; two would give a distribution, but a better distribution for purposes of statistical analysis is derived from subgroups step 1 which have for n at least four to seven individual readings set in step 1 or datum. The groups or sets specified in step 3 of subgroups specified in step 1 need only approach being consecutive and the failure to have the groups input be perfectly consecutive would not materially depart from the inventive concept herein.

An example of steps 9 through 10 would be as follows: Each data point or reading would be isolated in step 9(a) and 9(b) and grouped in subgroups of a size specified in step 1 of size n. In the preferred embodiment n could be equal to 5. This subgroup would then be selected step 10 by the user or by the program and the analysis which follows would take place.

For each subgroup selected in step 10 one of two steps would be available. Analysis step 11.0 or Medical specification step 11.1 for average step 11(a) and sigma (or range) step 11(b). If Medical specification is used, steps 12 through 14 may be skipped for purposes of generating control charts step 15 as set forth below.

Analysis step 11.0 of the data in the subgroup step 1 includes step 11(a) calculating an average (x-bar) and step 11(b) calculating the standard deviation (sigma). Calculating the range (R) of the set of the subgroup step 1 for purposes of graphing at a later time is an alternative to calculating sigma. Range is the statistical term for the difference between the highest reading in the subgroup from the lowest reading in the subgroup. Range is used to approximate sigma. Typically, the range is less accurate than sigma and therefore not desired.

This analysis step 11.0 would take place after each of the subgroups of step 1 selected in step 10 are collected, utilizing the process set forth above, keeping the units as close together as conveniently possible in order to have more or less continuous samples in a subgroup of step 1.

This information is stored 11(c), the average and standard deviation (or range) for purposes of graphing at a later time on a bar chart as described later.

Step 12 is a repetition of steps 9–11.0, usually with a delay set in step 2 for the sets step 3. The delay set in step 2 is usually accomplished by the programming but which may be a factor built into the sampling system due to delays in the computer equipment analyzing the data stream from the monitoring equipment. Having the sets set in step 3 too close together could result in covarlance with one reading affecting the next and this would mean the control limits would be too tight and would not give the body or the process being analyzed a chance to change. The delay 2 is a statistically significant delay 2 which would vary with the particular type of body reading, but is typically a very short time counted in seconds or portions of seconds.

The process above is repeated step 12 as set out until a statistically significant number of subgroups 1 are obtained. This number of subgroups is a set of a size specified in step 3 of size k. The true statistical number necessary would ultimately be obtained from observations over a number of patients. In the preferred embodiment set of step 3, k, is nine to twenty-five subgroups of a size specified in step 1 of size five. Fifteen is the value used for k below as an example.

Calculating control chart values step 13 would be for the purpose of setting the limits for obtaining a set of statistics charts known as control charts. This is done for an average (x-bar) control chart step 13(a) and a sigma control chart step 13(b). A range chart may be substituted for the sigma control chart.

Calculating step 13 involves taking all of the averages which are then averaged step 13(a) to obtain the average average (x double bar) for the twenty five subgroups. All of the set sigmas step 11(b), are averaged in order to get an average sigma (sigma bar) step 13(b) for the set of subgroups 1 (alternative to sigma average, all of the ranges step 13(c) may be averaged to get the average range (R-bar) for the set step 3 of subgroups step 1.

The sigma bar is obtained, for example, by adding up each sigma obtained step 13(b) and dividing by the number k in the set of size defined in step 3. For purposes of the discussion, it is assumed that this statistically significant number of repetitions of size defined in step 3 which are selected for this process is fifteen, and therefore sigmas one through fifteen are added up and then divided by fifteen in order to get sigma bar, or the average standard deviation. The average range and average average are determined using the same process. It can be noted at this time that the two control charts (e.g. sigma and average), though normally used together, are completely independent and the use of one chart without the other is statistically significant. FIGS. 1 through 9 show the average (or x-bar chart) displayed on a single screen below the sigma chart for three different sets of conditions.

Using the alternative step 11.1, the average-average, x-bar, and sigma are specified by the user, alleviating the need for steps 11 through 13 for generating control charts step 15. The purpose of medical specification 11.1 is described in more detail below.

The method for determining the value of sigma or sigma-bar for use of setting control chart limits is known in the art. As an example of the method, the derivation of sigma for an S or sigma chart could be according to a formula:

$$\sigma_S = [2(n-1) - 2n\ c_2^2]^{\frac{1}{2}} \cdot \frac{\sigma'}{\sqrt{2n}}$$

$\sigma'$ = population standard deviation p73
$\sigma_s$ = sample standard deviation
n = population size $$c_2 = (\sqrt{2/n}) \cdot \frac{\Gamma(n-2)}{\Gamma[(n-1)/2]}$$

$\Gamma$ = the gamma function:

$$\Gamma(x) = \int_0^\infty e^{-t}\ t^{X-1}\ dt,\ for\ 0 < x$$

An approximation is:

$$\sigma_S = \frac{\sigma'}{\sqrt{n_2}}$$

The upper and lower control limits and center lines are calculated as follows for 3 sigma:

$$c_2 = (\sqrt{2/n}) \cdot \frac{\Gamma(n-2)}{\Gamma[(n-1)/2]}$$

UCL = $\sigma + 3\ \sigma_s$
LCL = $\sigma - 3\ \sigma_s$
Center line = $\sigma_s$
$\sigma$ = average $\sigma$ As an example of the method, the derivation of sigma for an R or range chart would be:

$\sigma'' = \overline{R}/d$
$\overline{R}$ = average range
$d_2$ = standard deviation
UCL = $d_2\ \sigma'' + 3d_3\sigma''$
LCL = $d_2\ \sigma'' - 3d_3\ \sigma''$
Center line = $\overline{R}$ For X-bar charts, the control limits are calculated as follows:

$$UCL = x + 3\sigma''/\sqrt{n}$$

$$LCL = x - 2\sigma''/\sqrt{n}$$

Center line = $\overline{x}$
$\overline{x}$ = mean
$\sigma''$ = standard deviation
n = sample size.

These control limit sizes are known and tabled in the art. The factors to be used are loaded into the program as data to be used in the preferred embodiment as B conversion factors. For example, with sigma charts $B(2) = c_2 + 3\sigma_s/\sigma'$ and $B(1) = c_2 - 3\ \sigma_s/\sigma'$ and the B factors are previously obtained using tables known in the art.

The control limits are set step 14 for the charts using the sigma bar obtained. Statistically significant control limits usually utilized in industrial processes are three-sigma, as set forth above. Sigma factors are similarly derived from the preexisting art.

This user determination of sigma step 5(a) could be statistically as low as two (or lower), but would typically not be lower than two, and could be varied as high as four (or higher), or it could be any fraction between two and four, depending on what analysis of the particular data over time yielded. For purposes of most industrial processes, and therefore used in this example and in the preferred embodiment, the deviation 5(a) is three-sigma. Again, the specific value of the sigma factor used step 5(a) would depend on determinations which the user would make.

This process could be repeated for variable data, binomial data, and percentage data from the processes analyzed.

In the preferred embodiment, two charts are then generated step 15, the X-bar chart or average chart step 15(a), and a sigma chart 15(b). Sigma charts and R-charts reflect the same information which is often not significantly different. Range charts are only briefly discussed but could be substituted for sigma charts without departing from the inventive concept herein.

Each of the charts generated in steps 15(a) and 15(b) has an upper and lower control limit which was calculated step 14 using the sigma factors set by the user in step 5(a) set forth above and a middle line which is the sigma average (sigma bar) for the sigma chart step 15(b) and the range average (R-bar) for the range chart (alternate step 15(b)) and the average average (x-double bar) for the average chart 15(a).

An alternative step to step 15 is also available and is a major innovation possible with the invention. This would encompass the concept of stabilizing the patient within a set range and deviation which the user would select. This would be accomplished using medically specified average and sigma values step 11.1. Although identical to steps 15, steps of step 11.1 setting the average to be attained and setting the standard deviation to be attained and setting up control charts as set out in step 15 would provide control chart limits to which the user desired to bring the patient. This is not a normal statistical application but is available where a different stable condition is desirable within known control limits and where the patient's readings can be carefully changed. This would be a non-diagnostic use of the control charts and would be instead a method of treatment. Those charts step 15 could be used with the control charts.

The step 15 is to generate control charts steps 15(a) and 15(b). Although the preferred embodiment envisions the use of visible charts, the method works equally well if the charts are merely for purposes of analyzing data and are never actually displayed. This will be seen from the description which follows as to the use of the charts so generated.

Next it is necessary to identify step 16(a) and eliminate step 16(b) all possible instrumentation and non-medical outliers and eliminate the causes if possible. Experience has shown that it is usually necessary to make a trial run for each type of instrument used before applying the technique to an actual patient in order to eliminate non-medical causes for outliers. Once a system has been developed for a particular characteristic, this step is not required and is therefore not specific to all claims regarding the invention. This identification and elimination 16 steps 16(a) and 16(b) result in establishing control charts free of the identified outliers.

Control charts are then established on a change cause system, display step 17 of the control charts, free of as many non-medical causes of variation as possible. Control charts step 15 may be run in foreground (actual physical display on a screen or printed chart) or background (not physically displayed). FIGS. 1 through 9 show the results of foreground display of control charts of step 15.

If the charts are physically displayed in step 17, in the preferred embodiment it may be by a continuous graphing using a moving bar graph of the type known in the art. At least 30 points are usually desired on the screen, although more points or less may be desired and the actual number of points on a particular screen would vary and would be a function of the relevance of the history and abilities of the screen. As an example, if there were 15 minutes of relevant history and a high sampling rate, then 30 points is usually sufficient. Additionally, a script-type printout could be used in order to maintain a printout history.

Display step 17 requires that the data to be displayed be obtained. The data is obtained through the repetition of steps 9 through 11.0 followed by graphing the results against the control charts. Steps 9 through 11.0 are repeated step 12 throughout the monitoring process in order to provide the information needed for the display step 17.

The displaying step 17 may be broken down as indexing in a time scale step 17(a) a moving bar to the next position, step 17(b) calculating the position of average on the x-bar chart step, 17(c) calculating the position of sigma on the sigma chart, and identifying and marking statistically significant outliers step 17(d) (points outside control limits or points outside the theory of runs). This graphing step 17 is described in the discussion of FIGS. 1 through 9 below in more detail.

The sample rate may now change within limits without affecting the data which is produced. If the sample rate is too slow, possibly significant events could be missed and if the sample rate is too quick, the covariance problem resurfaces, as discussed above.

The speed with which data is displayed is such that the data should show the current condition of the patient, and that is what is strived for with any particular equipment.

The graphed samples of step 17 are obtained using the exact same steps set out in steps 9 through 11.0 in order to get the range, average and standard deviations of the subgroups.

Locating step 17(c) and marking step 17(d) points requires analysis. The analysis in locating step 17(c) is to analyze the point to be plotted relative to the middle line of the chart. The analysis in marking step 17(d) requires determining if the point is outside of the sigma limits set in step 5 using information calculated in steps 13 and 14 and whether the point violates the theory of runs 6. This is also discussed in the discussion of FIGS. 1 through 9.

Having at least two control charts, X-bar and sigma charts, in the preferred embodiment provides for two different methods of analysis for the information which is retrieved on a visual basis, which is not currently provided in medical technology. The first marking step 17(a) which is provided for in the two charts for a point outside of the control limits is circling the variant data and an audible tone may be given in order to allow the particular measurement which fell outside of the control limits to be noted.

An alternative would not display the actual graph (it would be run in the background) but display the occurrence of statistically significant indicators of change step 17.1. This could provide the same information without a constant display run in the foreground.

Because there is a continuous stream of this data, if a pattern appears of points outside the chart, it can be recognized and, similarly, if only a single individual reading falls outside, then it may be noted without having any reaction as a result of it.

Similarly, trends are shown by the X-bar chart as it moves in one direction, whereas destabilizations become more apparent with the R-chart or the sigma chart.

This method of interpreting patterns of variation on X-bar and R or sigma charts is documented in an industrial setting. Also, statistical analysis follows set patterns which these particular charts allow for the first time to be used in the medical field. However, the invention allows for the analysis and comparative use of information obtained from various patients over time, step 18, either as the treating physician noted a particular pattern which he wanted to review or on a continuous basis as specified.

Formulation of a database step 18 comprises the steps of step 18(a) isolating segments, as specified in step 7, of control charts, for example, a 30 item display of the patient, step 18(b) sending this segment to a database, step 18(c) medical database analysis and matching segments step 18(b) with database collection of similar segments and categorizing the same; comparing step 18(d) said portions to accepted treatments and diagnosis in a database; and grouping step 18(e) the sets of treatments and diagnosis with corresponding segments.

Once a complete comparison database step 18 is formed, data from a patient examined may be isolated step 19(a), the data sent to the same database step 19(b); statistical (as compared with medical) database analysis and matching pattern recognition step 19(c) of the portions step 19(a) of the control chart comparing the isolated portion to similar portions of control charts in the database, step 19(d) comparing the isolated portion or segment to the database collection of similar segments and categorizing the same and finally displaying step 19(e) diagnosis and treatment information from matched portions from the database to the user. The display may include the implementation of treatment.

Readjusting control limits comprises the readjustment of the control charts to changed conditions by repeating the steps 9 through 15 above as the patient's condition varies requiring new control charts.

FIGS. 1 through 9 show how information is interpretable either by a person monitoring the device or by electronically monitoring the device. In each FIGS. 1 through 9, the top Chart, e.g. FIG. 1(a) shows a normalized patient.

The average average, sigma bar and control limits for all three Charts, e.g. FIG. 1(a), FIG. 1(b) and FIG. 1(c), have been set according to these norms. That is steps 9-11.0 and 12 through 16 have been done only one time to formulate all three charts in each Figure.

The bottom Charts in each Figure, e.g. FIG. 1(b) and FIG. 1(c), show the same chart where the normalized patient control chart is still being used but either (a) the range for the average has been changed or (b) the range for the standard deviation has been changed slightly or (c) the range for the average and standard deviation have been changed slightly. These charts are artificially produced, but the same results are available from patient studies with the invention.

Analysis of all charts is similar. For purposes of the discussion, only Charts on FIG. 1 are specifically discussed. The same analysis applies to FIGS. 1 through 9.

The chart features, generated in steps 9 through 15 are given numerically as well as graphically. The chart shows the upper control limit (three sigma is used) 32 which is three sigma above the average average middle line 33 on the chart representing the average average or x-bar from step 14(a). The upper control limit numerically displayed 32 is graphically displayed as a UCL line 48. The average average middle line 33 is displayed as the average line 49. The lower control limit numeric display 34 is displayed as a LCL line 50 opposite the average line 49 from the UCL line 48.

Below the x chart described above is the sigma chart. The sigma chart has the upper control limit 35 (three sigma from step 14(b) above the centerline 36), the center 36 is sigma bar from step 14(b), the lower control limit is 37 is opposite the center line 36 from the upper control limit 35. The display shows a UCL line 51 for the upper control limit 35, a LCL line for the lower control limit 35 and a center line 52 for the center 36.

The blank 47 shown in FIG. 1(a) running perpendicular to the center lines of both charts represents the index location step 17(a) of the plotter, where the next point is to be plotted. Along the bottom are specification for the number of subgroups 1 plotted, zero 38, ten 39, twenty 40, thirty 41, forty 42, fifty 43, and sixty 44. The top irregular line 45 represents the graphed appearance of the average of subgroups 1. The bottom irregular line 46 in FIG. 1(a) represents the appearance of sigma for subgroups 1.

Figure 5A:
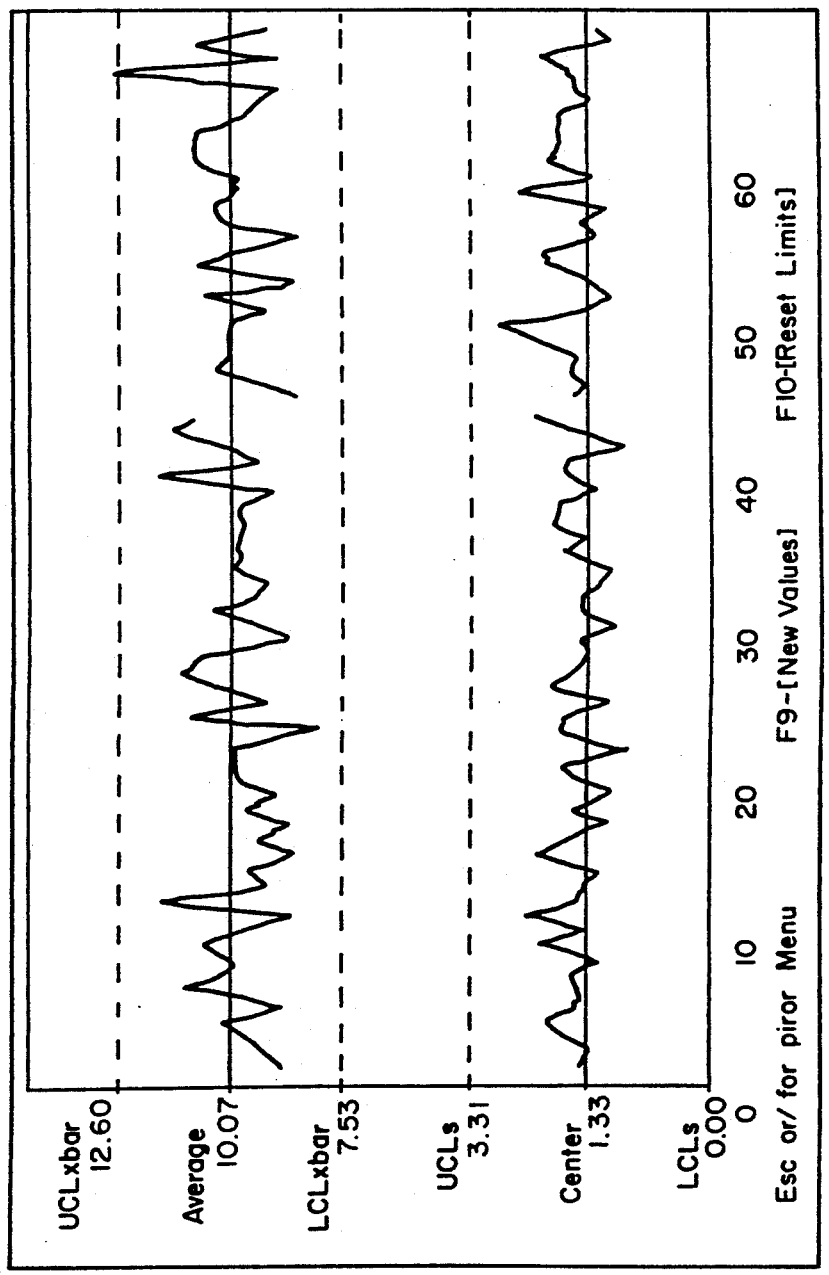
FIGS. 5A, 5B, and 5C are a graphical representation of a set of three charts generated by the system showing the effect of a change of standard deviation with an increasing change of average.
Figure 5B:
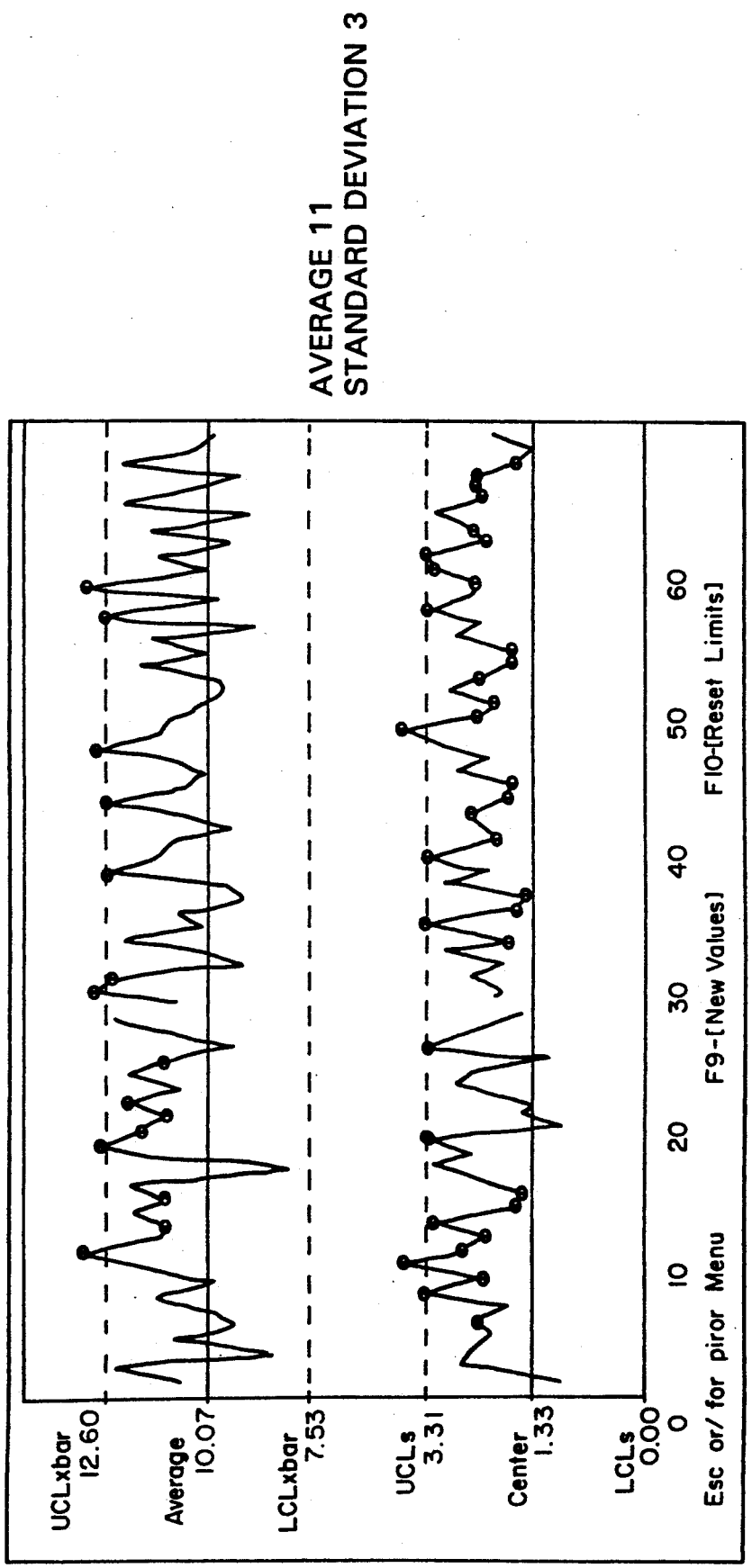
Figure 5C:
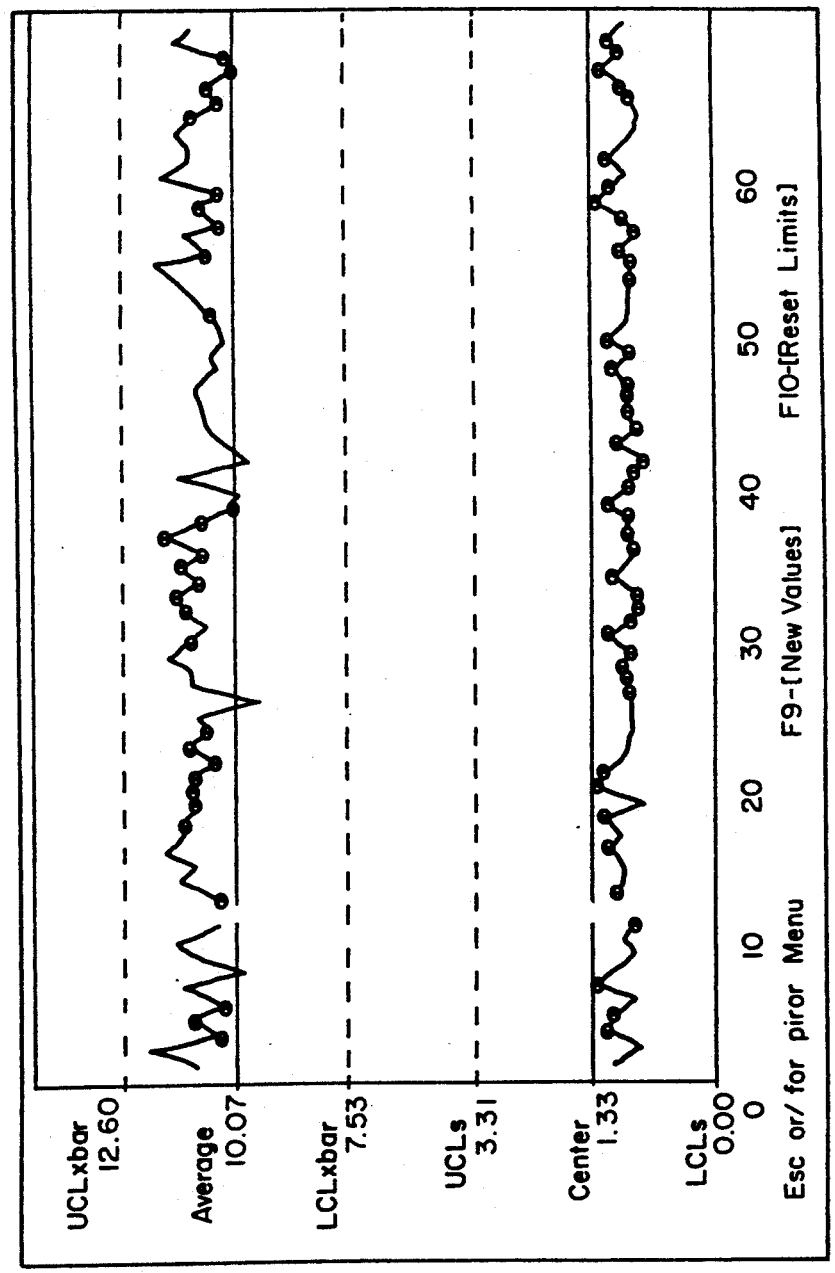
Figure 6A:
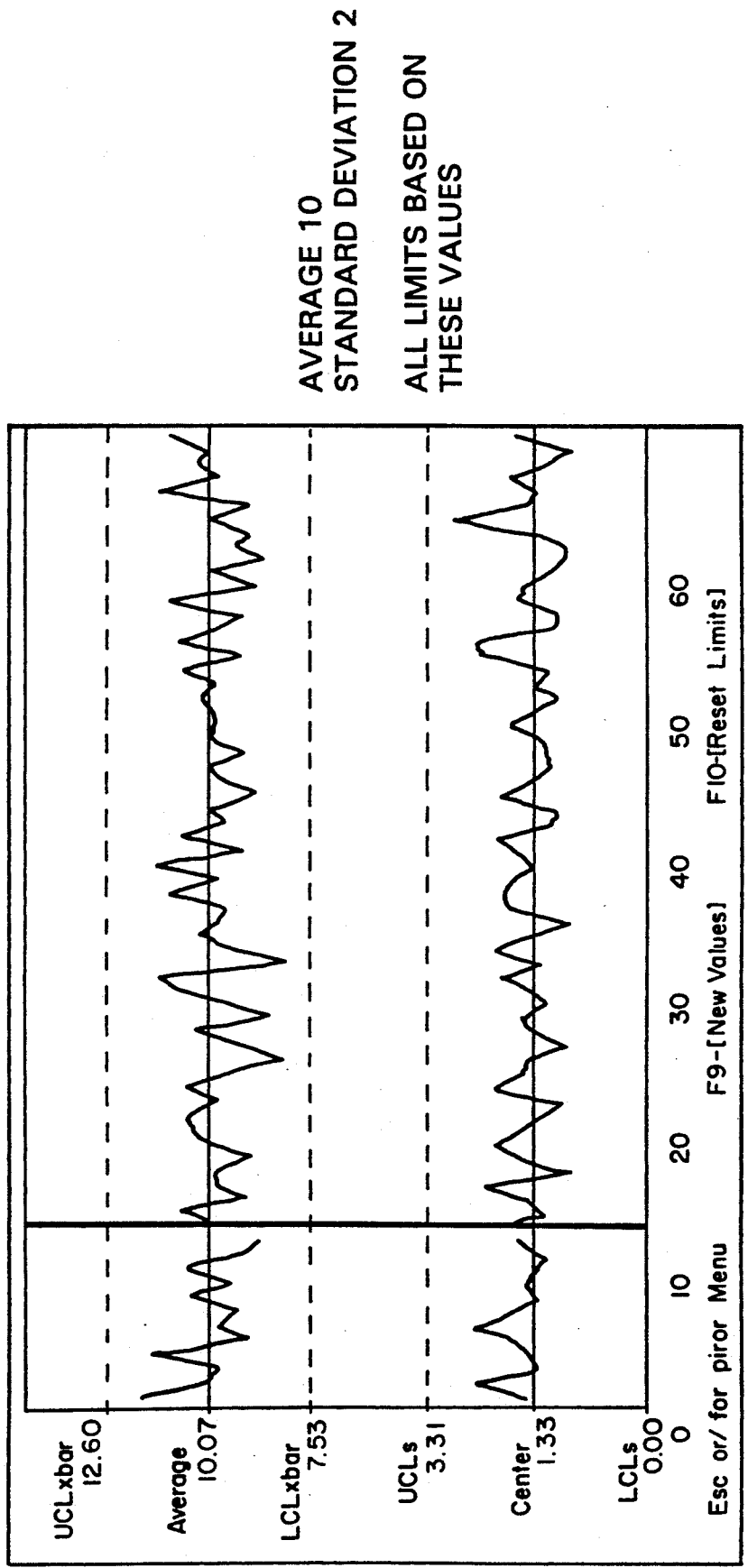
FIGS. 6A, 6B, and 6C are a graphical representation of a set of three charts generated by the system showing the effect of a change of standard deviation with a decreasing change of average.
Figure 6B:
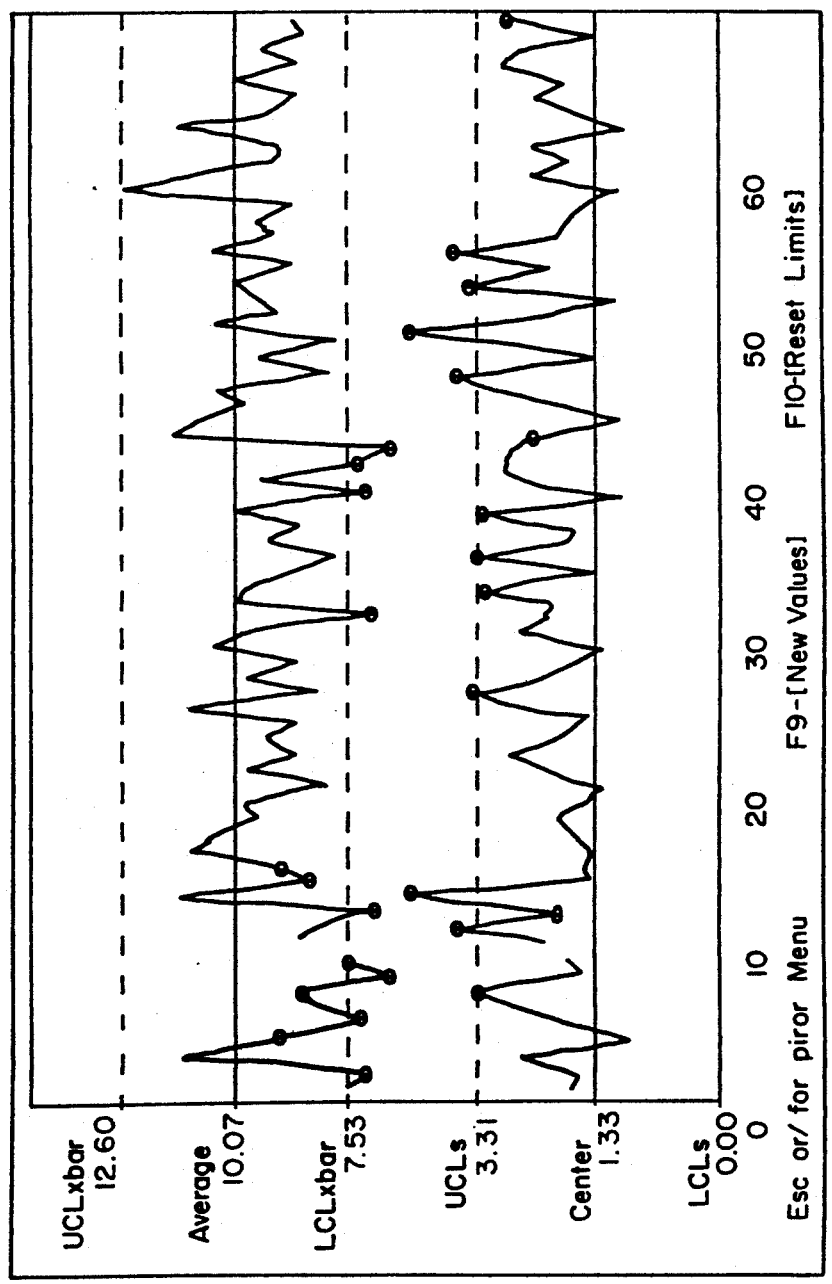
Figure 6C:
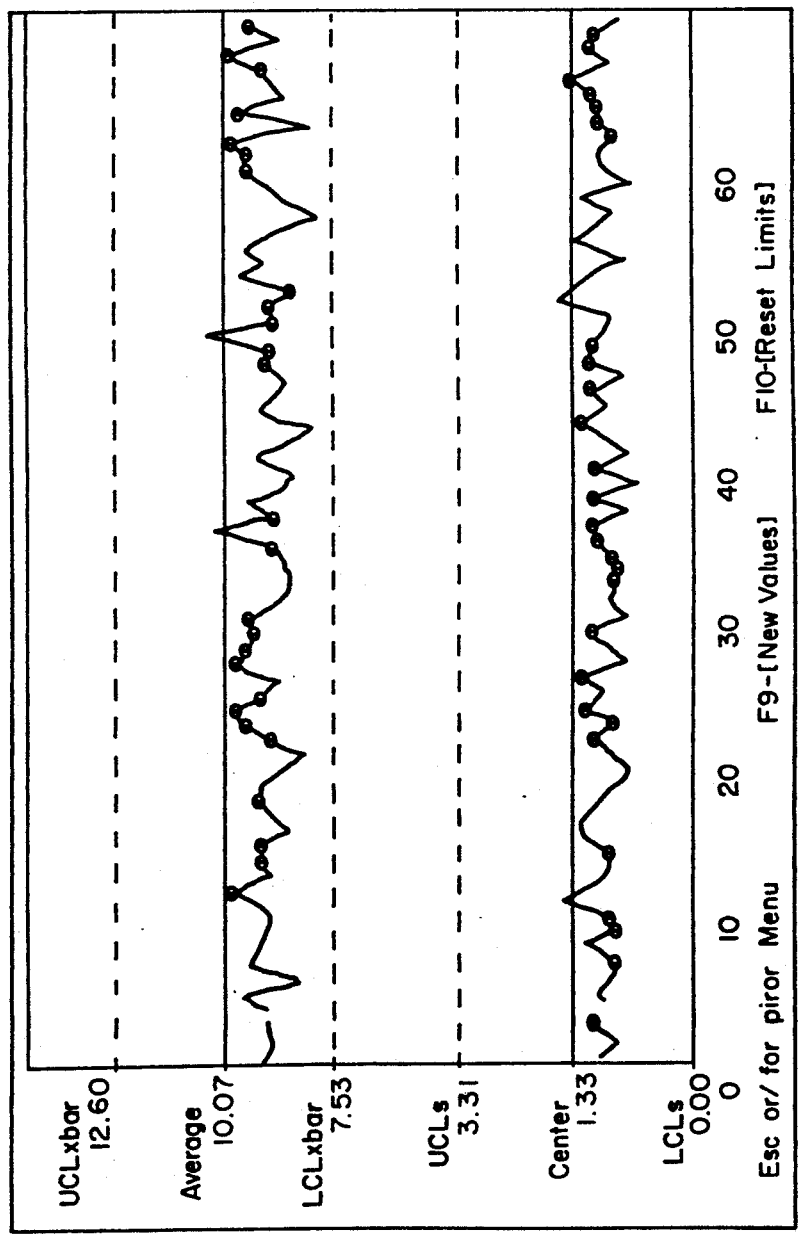
Figure 7A:
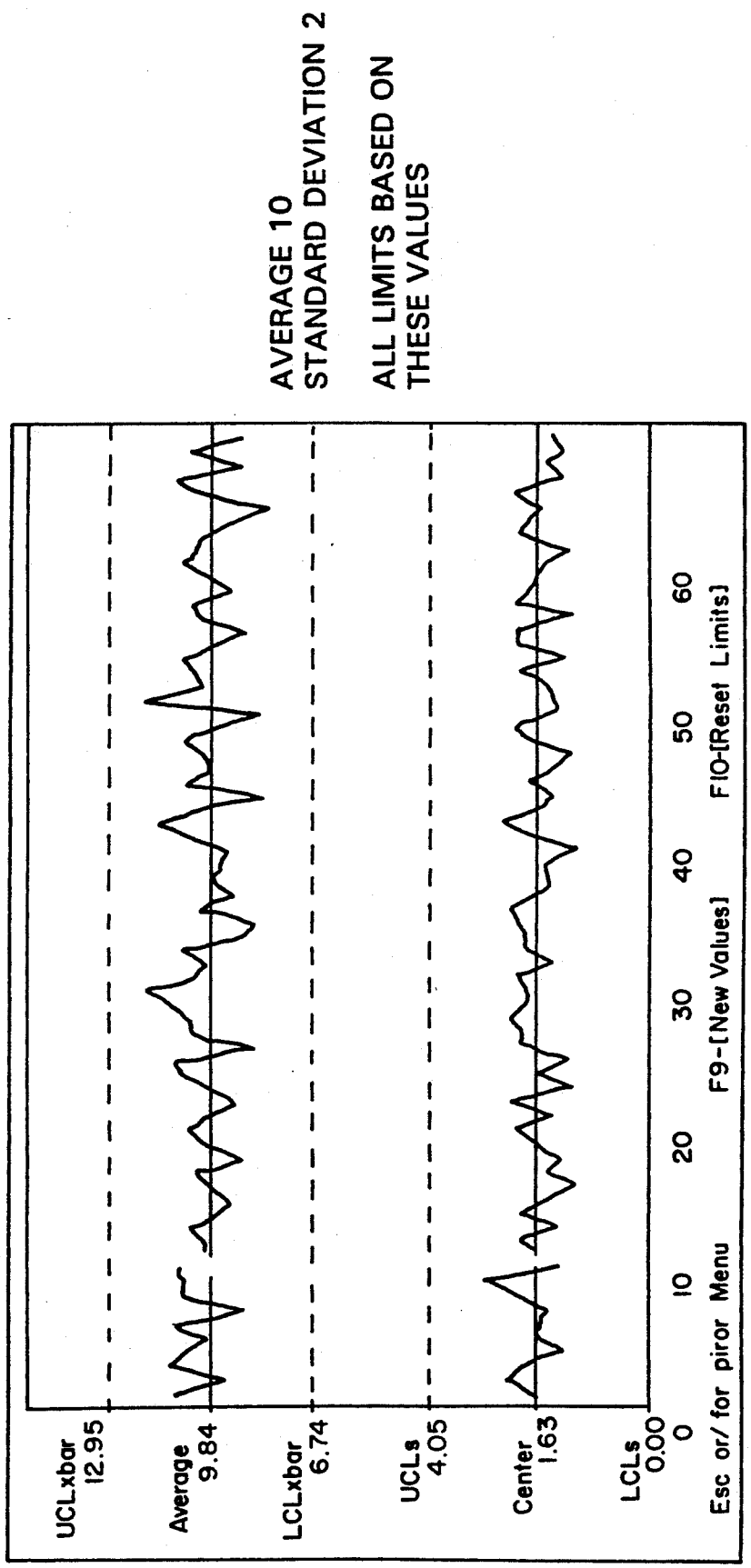
FIGS. 7A, 7B and 7C are a graphical representation of a set of three charts generated by the system showing the effect of a change of average without a change of standard deviation.
Figure 7B:
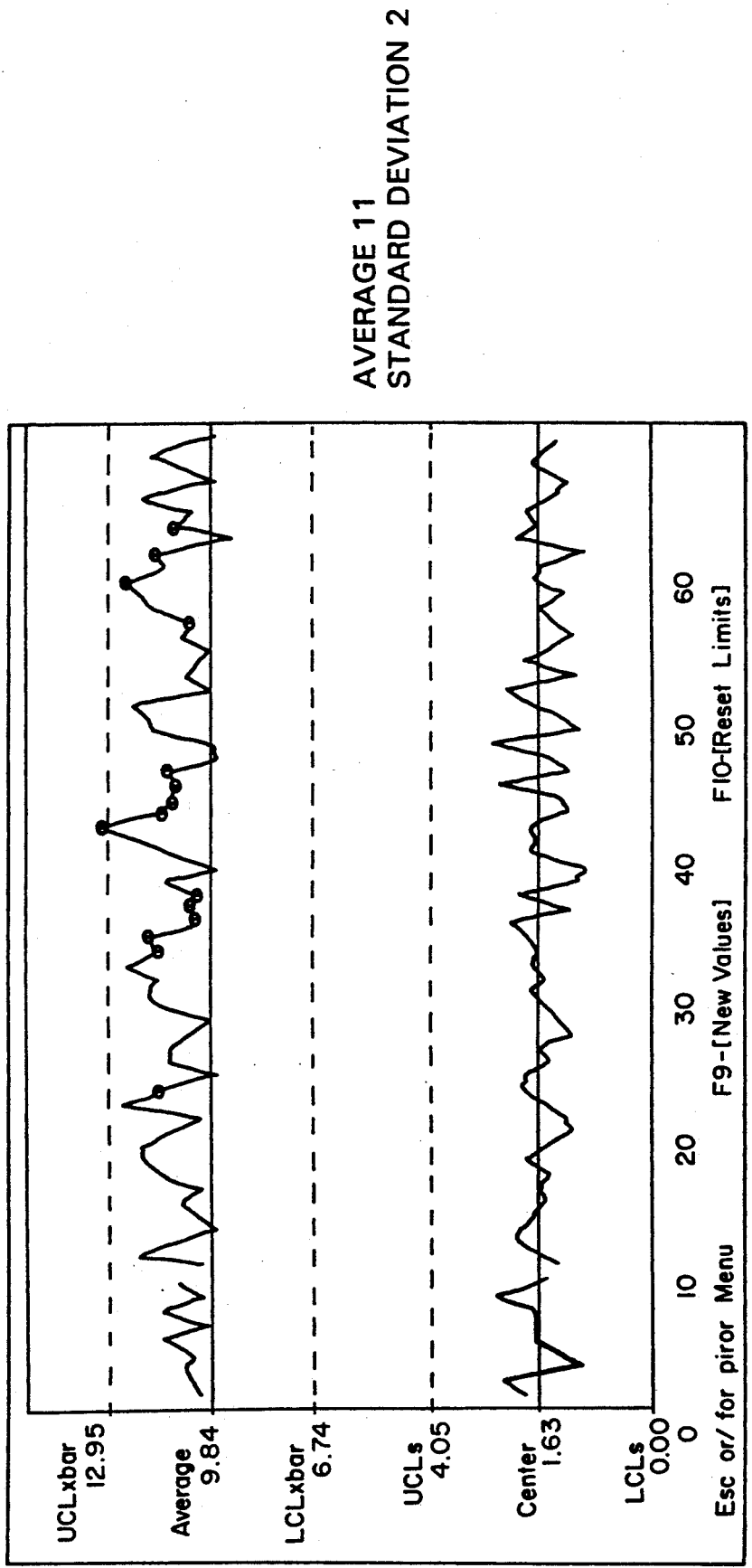
Figure 7C:
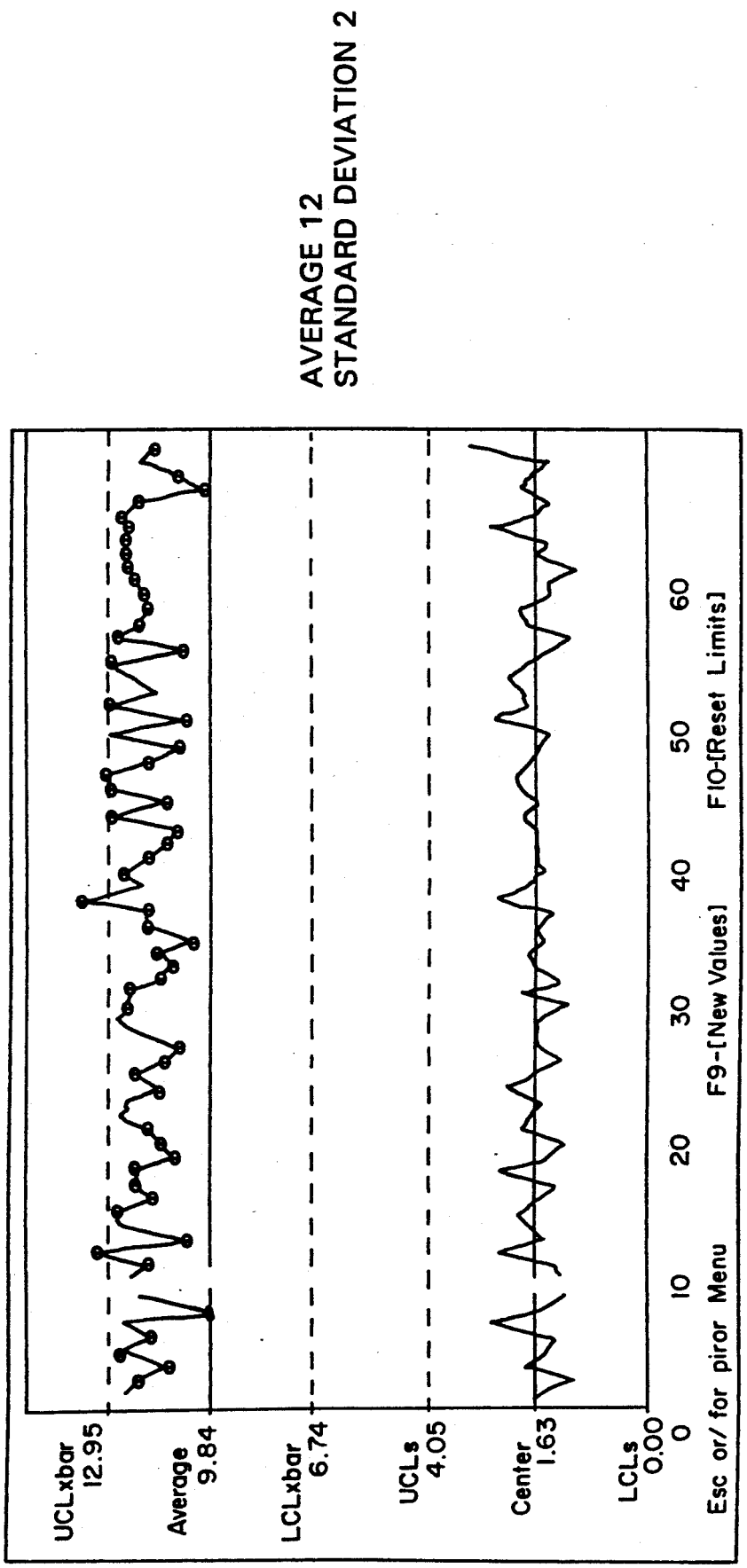
Figure 8A:
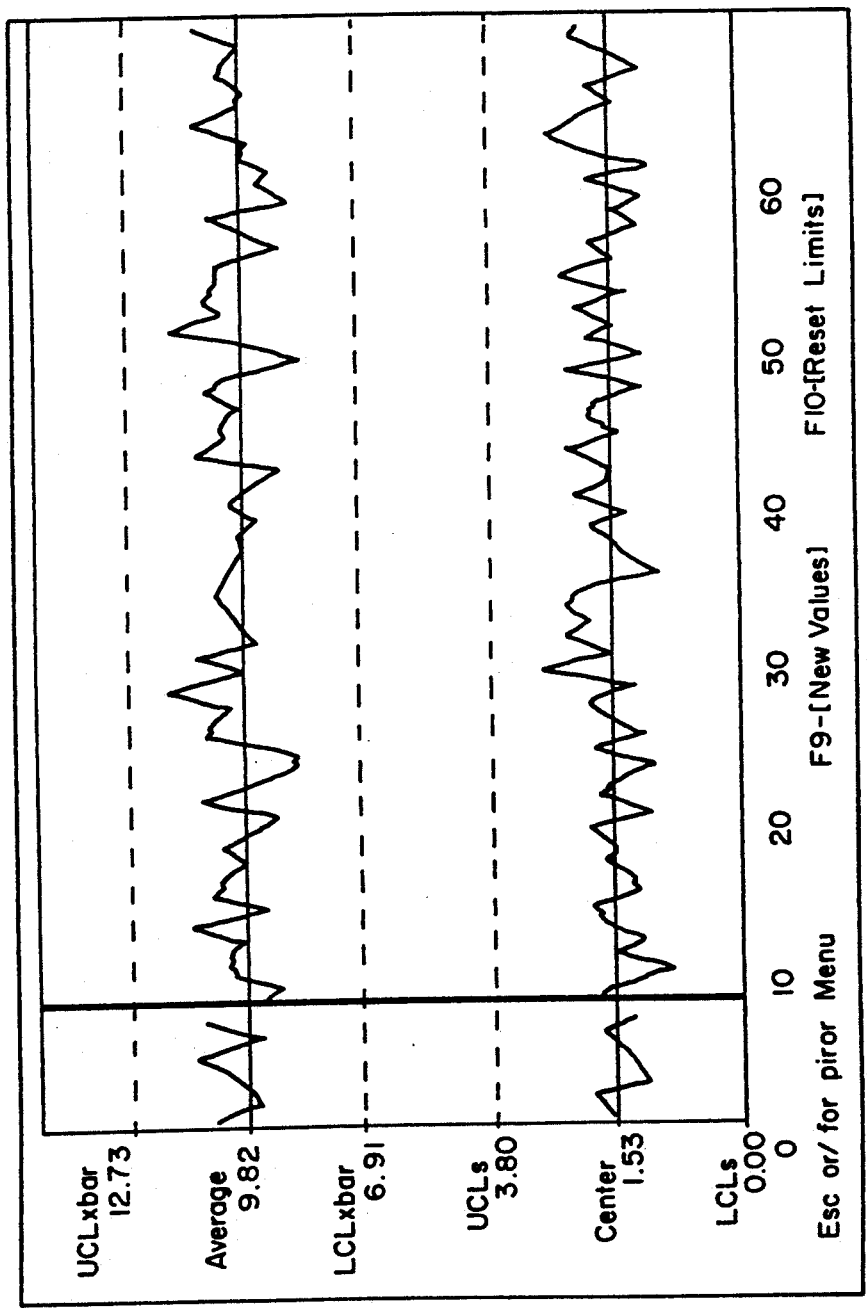
FIGS. 8A, 8B, and 8C are a graphical representation of a set of three charts generated by the system showing the effect of a change of standard deviation without a change of average.
Figure 8B:
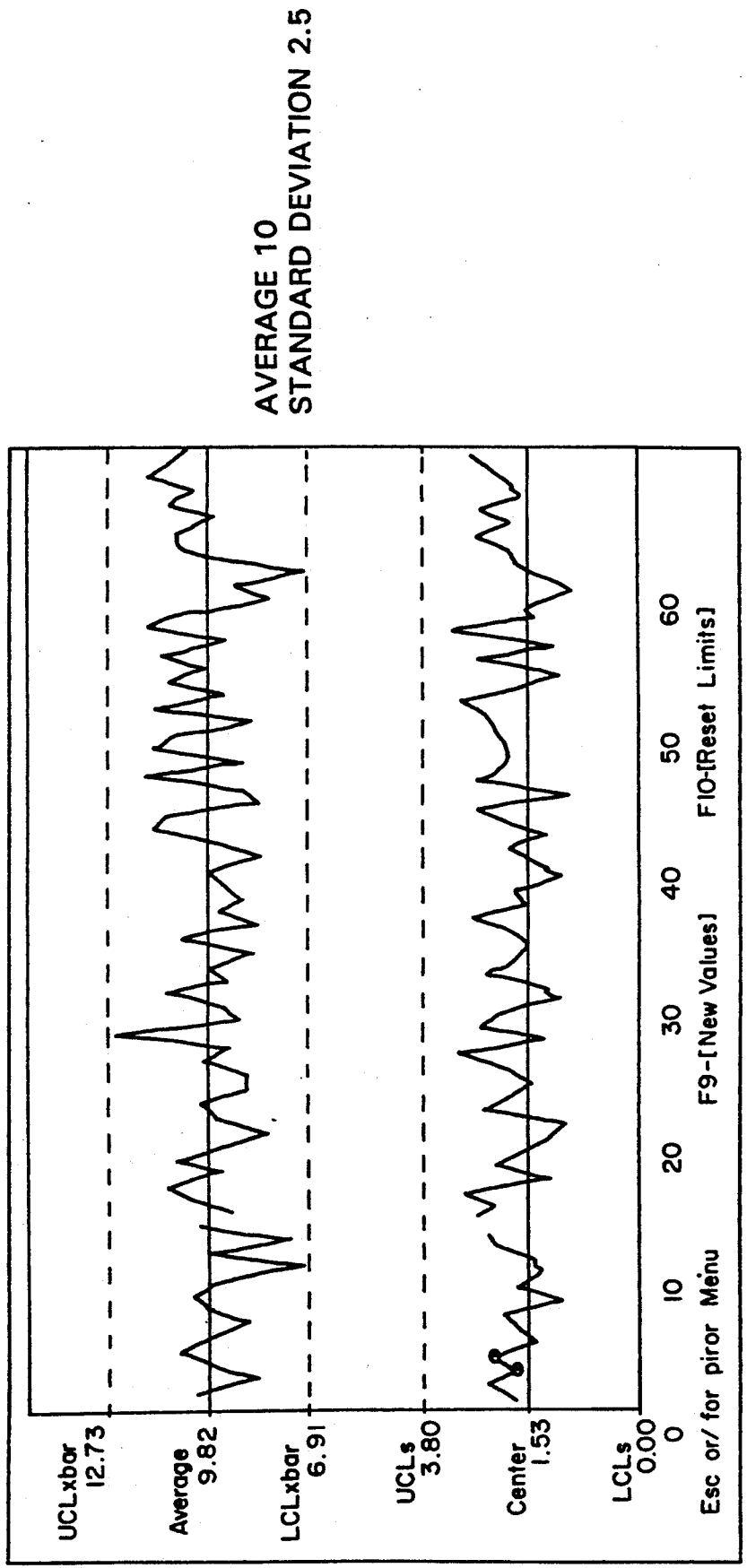
Figure 8C:
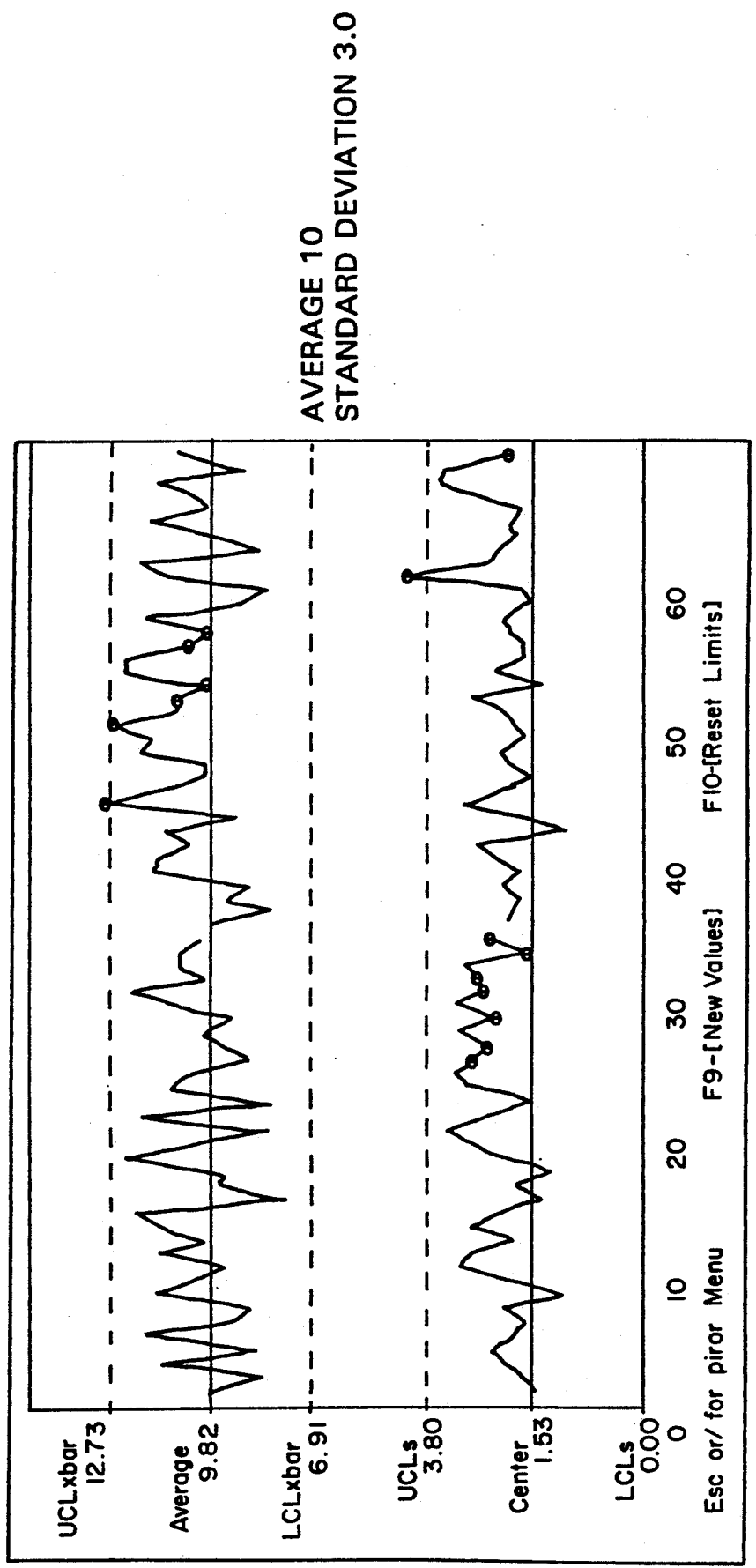
Figure 9A:
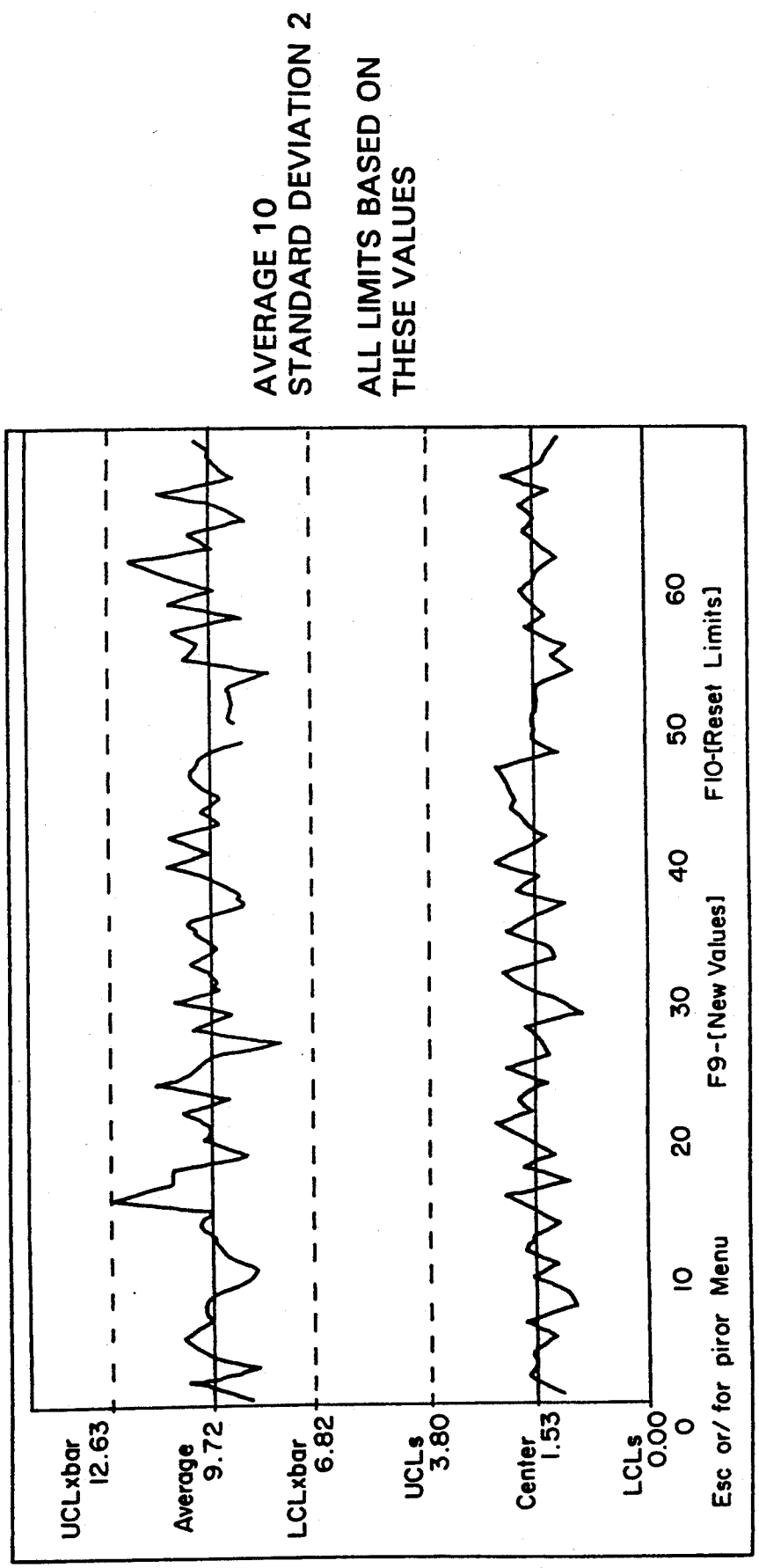
FIGS. 9A, 9B, and 9C are a graphical representation of a set of three charts generated by the system showing the effect of a change of average without a change of standard deviation.
Figure 9B:
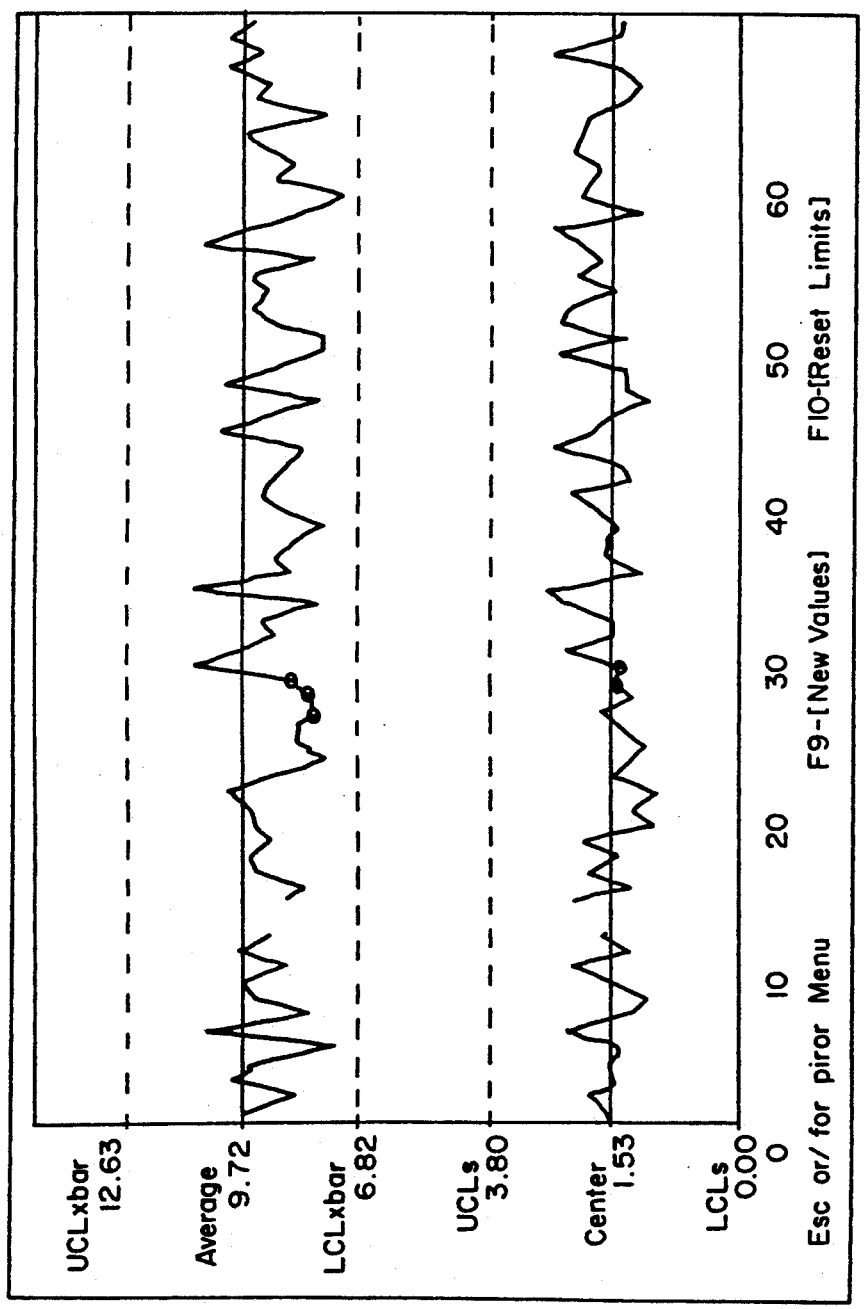
Figure 9C:
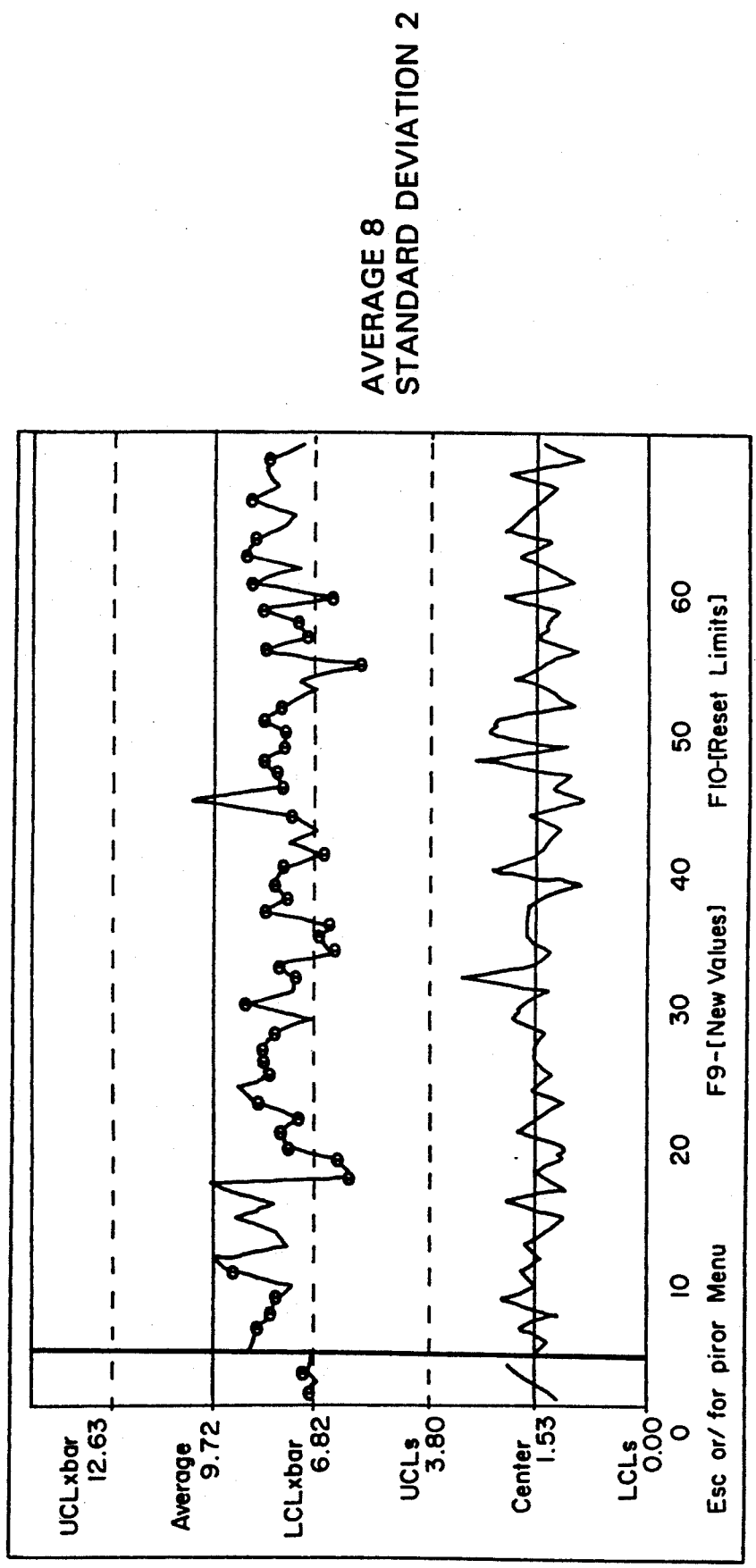

To the side of each of the charts in FIG. 5 are specifications for Average and Standard Deviation. Specified Average 26 and specified Standard deviation 27 are used to generate charts appearing in FIGS. 1(a), 1(b) and 1(c). The top irregular line 45 and bottom irregular line 46 in FIG. 1(a) also uses specified average 26 and specified standard deviation 27. In FIG. 1(b), top irregular line 45 and bottom irregular line 46 use specified average eleven 28 and specified standard deviation 29. In FIG. 1(c), top irregular line 45 and bottom irregular line 46 use specified average twelve 30 and specified standard deviation two 31.

Charts in FIG. 1(a) represent the normalized patient. FIGS. 1(b) and 1(c) show the function of the invention as the patient varies from the normalized state. High point 54 shows a subgroup 1 having an average (x-bar) 11(a) greater than the upper control limits 14(a) and therefore marked by a circle. Run point 55 shows a subgroup 1 which follows a number of subgroups which consecutively are above the average line 52 without a break for a point below the average line 52.

Circled points on FIGS. 5 through 13 show where the readings have exceeded either the control limits (above the dotted lines) or have exceeded the theory of runs, more than a certain number of readings on one side of the average.

FIGS. 1(a) through 9(a) show similar normalized charts. Deviations as indicated on the respective charts are shown in FIGS. 1(b) through 9(b) and 1(c) through 9(c). These are provided in an effort to show the product resulting from the use of the invention.

Although the sigma factor is usually the same for the upper and lower control limits on either chart, it may be varied for each separately in step 1(a) without departing from the inventive concept and this may prove desirable for certain situations. The average upper control limit 48, the lower average control limit 50, and the upper sigma control limit 51 are displayed as dotted lines. The lower sigma control limit 53, x-bar line 45, and sigma bar line 52 are displayed as a solid line. The dotted line is merely a helpful method of display and solid lines may also be dotted. The lines may be displayed in different colors, shapes, etc. without departing from the original concept.

Each of FIGS. 1-9 show three sets of two control charts. The two control charts in the upper set of each figure shows the normalized patient graph as set up using steps 1-17 above. The average and standard deviation used in establishing these charts is indicated at the right of the chart for instructional purposes.

The next two charts in each of FIGS. 1 through 9 show what is displayed when using the same charts but varying average and standard deviation as shown to the right. The step 17 is applied only to the existing control charts. The statistically significant variations are shown as circled marks in the display. Although any number of variations is possible on a given patient, these displays are instructional as to showing what may occur given various changes.

It is an additional improvement over the prior art arising from the disclosure that different confidence levels, upper and lower control limits and theory of runs, may be used at once. As shown in FIG. 11A steps 5 and 6. These confidence levels could be used so that when the first control limit was reached below or above the midline, an alarm would sound; and when the second control limit was reached, farther from the midline than the first, action would be dictated. Similarly, information could be sent to the database for comparison after the first was reached, and treatments and diagnosis displayed upon reaching the second.

One use of the techniques developed herein would be for monitoring the effectiveness of displays on equipment. Either using separate equipment with the equipment to be tested or merely using the equipment to be tested, a statistical analysis of the equipment to be tested could be conducted. In this way, on a single time line, the statistical information from the control chart could be plotted along with the display information from the equipment to be tested. A comparison of the two would show the effectiveness of the equipment.

Because many varying and different embodiments may be made within the scope of the inventive concept herein taught and because many modifications may be made in the embodiment(s) herein detailed in accordance with the descriptive requirements of the law, it is to be understood that the details herein are to be interpreted as illustrative and not in a limiting sense.

We claim:

1. The process of monitoring patient vital signs from a monitoring device which is generating data using control charts with at least one control chart limit comprising the steps of:
   (a) collectioning said data from said monitoring device;
   (b) placing said data into statistically significant subgroups of at least one datum each;
   (c) calculating for said statistically significant subgroups statistics to graph against said control charts;
   (d) repeating the process steps (a) through (c) continuously;
   (e) selecting for a statistically significant number of repetitions of steps (a) through (c) the data necessary to set at least one control chart limit;
   (f) setting at least one control chart limit with said data;
   (g) setting up at least one control chart with said at least one control chart limit;
   (h) continuously graphing said statistics against said at least one control chart making a diagnosis or performing a treatment on said patient using said monitored vital signs graphing statistics.

2. The process of claim 1 wherein the statistically significant subgroups are consecutive.

3. The process of claim wherein the control chart limit comprises at least one upper control limit.

4. The process of claim 3 wherein the control chart has at least one lower control limit.

5. The process of claim 1 wherein the control chart limit comprises at least one lower control limit.

6. The process of claim 1 wherein the control chart comprises at least one midline.

7. The process of claim 6 wherein there is a first and second different control limit on a single side of the control chart, midline being a first control limit and second control limit and wherein one of the two control chart limits is farther out than the other control limit.

8. The process of claim 7 comprising the additional step of giving a warning signal when the first control limit is reached.

9. The process of claim 8 comprising the additional step of directing a separate action when the second limit is reached.

10. The process of claim 7 wherein the information is sent to a database after the first control limit is reached.

11. The process of claim 1 wherein the control chart has a midline, at least one upper control limit and at least one lower control limit.

12. The process of claim 1 wherein the process includes the additional step of (1) marking statistically significant deviations.

13. The process of claim 1 wherein the statistics comprise the average and the standard deviation (sigma) for each of the statistically significant subgroups.

14. The process of claim 13 wherein the step of selecting for a significant number of repetitions the data necessary to set said control chart limits comprises the additional step of calculating the average of the averages (x-double bar) and the average of the standard deviations for said statistically significant number of repetitions.

15. The process of claim 1 comprising the additional step of:
   (i) readjusting the control chart limits by repeating the steps (a)-(g) for originally setting the control chart limits as set forth above as the patient's condition varies requiring new control charts.

16. The process of claim 1 comprising the additonal steps of:
   (i) sending data from the first isolated portion of a first control chart to a database;
   (j) categorizing said first isolated portion to the database collection of similar segments and categorizing by similarity;
   (k) grouping said first isolated portions with medical data in said database;
   (l) comparing said first isolated portion in said database to second portions of a second control chart so as to match said second control chart portion to the first database portion; and
   (m) displaying the accepted medical data with said portion first.

17. The process of claim 16 wherein the medical data comprises treatment.

18. The process of claim 16 wherein the medical data comprises diagnosis data.

19. The process of claim 1 wherein (a) further comprises the steps of:
   (I) selecting data from the stream of data originating from the monitoring device;
   (II) compartmentalizing data into records;
   (III) isolating that datum of each selected record related to the monitored vital sign.

20. The process of claim 20 wherein the graphing further comprises matching each subgroup with an associated time.

21. The process of claim 20 wherein the device has a device display and comprising the additional step of comparing the display of the monitoring device against the control charts to determine the reliability of the monitoring device display.

22. The process of claim 20 further comprising the step of graphing the control chart using a time dependent scale to mark the distances between markings.

23. The process of claim 1 wherein step (g), setting up at least one control chart, further comprises:
   a. selecting of standards from a present group;
   b. selecting the at least one control chart from the following set:
      (i) Average charts
      (ii) Range charts
      (iii) P charts, percent effective or defective
      (iv) U charts, defect charts
      (v) C charts, defect per instance charts
      (vi) NP charts, number of occurrences charts
      (vii) sigma charts.

24. The invention of claim 23 wherein the sigma and average chart are used together and wherein the invention comprises the additional steps of:
   a. determining at least one of the following standards: the size of the sample subgroup, the method for introducing delay, the number or set of subgroups, the statistical method to be used, the confidence level for entering limits, the confidence level for action limits, setting the theory of runs.

25. The process of claim 24 wherein a range chart is substituted for the sigma chart.

26. The process of claim 23 wherein steps (a) through (h) further comprise:
   i. Inputting of data;
   ii. compartmentalization of data into records;
   iii. grouping of preferably consecutive data into subgroups;
   iv. finding an average (x-bar) and finding the standard deviation (sigma) for each subgroup;
   v. storing the x-bar and sigma;
   vi. Repeating steps i through ii continuously with a delay selected by the user;
   vii. selecting a statistically significant number of subgroups;
   viii. calculating control chart values for an average (x-bar) control chart for a sigma control chart;
   ix. generating two charts, an x-bar chart or average chart, and a sigma chart;
   x. continuously graphing information from step s on the charts.

27. The process of claim 23 wherein the step of determining the average-average, x-double bar, and sigma is replaced with the step of specifying x-double bar and sigma bar.

28. The process of claim 27 comprising the additional step of stabilizing the patient to a set range and deviation for medically specified average and sigma values.

29. The process of claim 23 wherein the step of setting up a control chart limit comprises the additional steps of identifying all possible instrumentation and non-medical outliers and eliminating the causes if possible establishing control charts free of the identified outliers and eliminating all possible instrumentation and non-medical outliers.

30. The process of claim 1 wherein the entire process is used for at least two of the following data types known in the art: variable data, binomial data, and percentage data from the processes analyzed.

31. The process of claim 1 wherein the chart features generated are shown numerically.

32. The process of claim 31 wherein chart and numeric display comprises:
   a. at least one of either a sigma chart or a range chart or an x-bar chart;
   b. numeric displays of the upper and lower control limit and midline the same being displayed numerically beside the graphical display for both the x-bar chart and the sigma chart.

33. The process of claim 1 wherein the statistics comprise the average and the range for each of the statistically significant consecutive subgroups.

34. The process of claim 33 wherein the step of selecting for a significant number of repetitions the data necessary to set said control chart limits comprises the additional step of calculating the average of the averages (x-double bar) and the average of the ranges for said statistically significant number of repetitions.

35. The process of claim 33 further comprising the step of displaying the results on the time dependent scale so that each subgroup is matched with the associated time.

36. A method of monitoring a patients's vital signs comprising the steps of:
   (a) examining a patient to get data;
   (b) isolating data from a patient;
   (c) sending the data to a database;
   (d) statistically (as compared with medical) analyzing the data relative to the database;
   (e) matching pattern recognition of the portions of the control chart comparing the isolated portion to similar portions of control charts in the database;
   (f) comparing the isolated portion or segment to the database collection of similar segments and categorizing the same; and
   (g) displaying diagnosis to the user.
   (h) using said diagnosis and treatment information to make a diagnosis or perform a treatment on said patient.

37. The process of the claim 36 comprising the additional step of implementation of treatment displayed.

38. A method of analyzing data from new medical patients comprising the following steps:
   a. determining the number of consecutive runs;
   b. determining factor times for an x-bar chart, standard deviation chart, and range chart for upper and lower control limits;
   c. determining number of data samples to be used in each sub-group;
   d. determining number of repetitions for sampling for determining the average standard deviation on midline for the sigma, range, and average control charts;
   e. determining sample rates;
   f. inputting data;
   g. compartmentalizing data into records;
   h. isolating significant portions of each record for graphing on control charts;
   j. selecting consecutive subgroups of statistically significant size;
   k. calculating the average, standard deviation, and range for each subgroup;

l. pausing as necessary to avoid co-variance between subgroups;
m. repeating steps of selection, calculating, and pausing for a number of repetitions set by the user in step (d) above;
n. averaging the averages over all subgroups, standard deviation over all subgroups, and range or standard deviation over all subgroups for the number of repetitions;
o. setting control limits by multiplying the B factor times the average sigma in order to determine the upper and lower control limits;
p. set up control charts utilizing the averages for averages, standard deviations, and ranges calculated above;
q. continuously repeating the steps of input of data, compartmentalization of data, isolation of significant portions of records, selecting consecutive subgroups, calculating the average, standard deviation, and range;
r. continuously graphing on or against a control chart and displaying on a control chart each of the consecutive subgroups;
s. marking deviations as to the theory of runs as set out above, subgroups whose statistical information goes over the control limits;
t. readjusting the control limits as desired;
u. isolating segments of the control charts;
v. comparing isolated portions of the control charts to similar isolated portions of the control charts in a database;
w. displaying and using said isolated portions and said similar isolated portions to make a diagnosis or perform a treatment on said patients.

* * * * *